US009143393B1

(12) United States Patent
Bird et al.

(10) Patent No.: US 9,143,393 B1
(45) Date of Patent: Sep. 22, 2015

(54) SYSTEM, METHOD AND APPARATUS FOR CLASSIFYING DIGITAL DATA

(75) Inventors: Robert Bird, Longwood, FL (US); Greg Barton, Longwood, FL (US); Matthew Whitlock, Longwood, FL (US)

(73) Assignee: Red Lambda, Inc., Longwood, IL (US)

( * ) Notice: Subject to any disclaimer, the term of this patent is extended or adjusted under 35 U.S.C. 154(b) by 464 days.

(21) Appl. No.: 13/351,780

(22) Filed: Jan. 17, 2012

Related U.S. Application Data

(63) Continuation-in-part of application No. 10/852,776, filed on May 25, 2004.

(60) Provisional application No. 61/432,795, filed on Jan. 14, 2011, provisional application No. 61/489,535, filed on May 24, 2011, provisional application No. 61/567,408, filed on Dec. 6, 2011.

(51) Int. Cl.
*G06F 15/16* (2006.01)
*H04L 12/24* (2006.01)
(Continued)

(52) U.S. Cl.
CPC .......... *H04L 41/046* (2013.01); *G06K 9/00442* (2013.01); *G06K 9/46* (2013.01);
(Continued)

(58) Field of Classification Search
CPC ... G06N 3/0436; G06K 9/00442; G06K 9/46; G06K 9/6202; G06K 9/6248; Y10S 707/99945; Y10S 707/99932; Y10S 707/99933; G06F 19/28; G06F 19/12; G06F 19/26; H04L 41/046; H04L 41/0631; H04L 41/0893
USPC ............... 709/247, 224; 706/1, 20; 707/3, 707/999.003; 382/218
See application file for complete search history.

(56) References Cited

U.S. PATENT DOCUMENTS 6,047,277 A   4/2000   Parry et al.
6,077,305 A   6/2000   Cheng et al.
(Continued)

FOREIGN PATENT DOCUMENTS

CN   101315644   12/2008
EP       1026867   8/2000
WO   WO 2011/077013   6/2011

OTHER PUBLICATIONS

Wuzuo Wang et al. "Online Detection of Network Traffic Anomalies Using Degree Distributions". Journal: International Journal of Communications, Network and System Sciences . 2010. vol. 03, Iss: 02 , pp. 177-182 URL:http://www.doaj.org/doaj?func=abstract&id=780425&q1=network%20event&f1=all&b1=and&q2=&f2=all&recNo=2&uiLanguage=en.
(Continued)

*Primary Examiner* — Kyung H Shin
(74) *Attorney, Agent, or Firm* — William G. Giltinan; Carlton Fields Jorden Burt, PA

(57) ABSTRACT

A data classification system comprising a server adapted to receive data elements from a computer network, compute a distance between the elements and a plurality of representative elements such that where the distance is less than a threshold, the input elements are associated with the representative element and where the distance is not less than the threshold, the input element is stored as a new representative element. A method of classifying network traffic is further disclosed that can include providing a server adapted to receive data from a network, compute a distance between the data elements and representative data elements such that where the distance is less than a threshold, the input elements are associated with the representative element and where the distance is not less than the threshold, the input element is stored as a new representative element.

51 Claims, 10 Drawing Sheets

(51) Int. Cl.
  *G06K 9/62* (2006.01)
  *G06N 3/04* (2006.01)
  *G06K 9/46* (2006.01)
  *G06K 9/00* (2006.01)
  *G06F 19/28* (2011.01)
  *G06F 19/26* (2011.01)
  *G06F 19/12* (2011.01)

(52) U.S. Cl.
  CPC ........... *G06K 9/6202* (2013.01); *G06K 9/6248* (2013.01); *G06N 3/0436* (2013.01); *H04L 41/0631* (2013.01); *H04L 41/0893* (2013.01); *G06F 19/12* (2013.01); *G06F 19/26* (2013.01); *G06F 19/28* (2013.01)

(56) References Cited

U.S. PATENT DOCUMENTS

| | | | |
|---|---|---|---|
| 6,219,786 B1 | 4/2001 | Cunningham et al. | |
| 6,654,782 B1 | 11/2003 | O'Brien et al. | |
| 6,728,695 B1 | 4/2004 | Pathria et al. | |
| 6,904,420 B2 * | 6/2005 | Shetty et al. | 706/1 |
| 7,017,186 B2 | 3/2006 | Day | |
| 7,164,797 B2 * | 1/2007 | Simard et al. | 382/218 |
| 7,295,831 B2 | 11/2007 | Coleman et al. | |
| 7,337,106 B2 | 2/2008 | Liu | |
| 7,363,656 B2 | 4/2008 | Weber et al. | |
| 7,376,635 B1 | 5/2008 | Porcari et al. | |
| 7,469,418 B1 | 12/2008 | Wilkinson et al. | |
| 7,509,578 B2 | 3/2009 | Rujan et al. | |
| 7,519,860 B2 | 4/2009 | Hatonen et al. | |
| 7,586,871 B2 | 9/2009 | Hamilton et al. | |
| 7,796,029 B2 | 9/2010 | Ma et al. | |
| 7,801,748 B2 | 9/2010 | Bonissone et al. | |
| 7,877,477 B2 | 1/2011 | Wookey | |
| 7,908,357 B2 | 3/2011 | Goranson et al. | |
| 7,953,594 B2 | 5/2011 | Jeong et al. | |
| 7,962,611 B2 | 6/2011 | Hurley et al. | |
| 8,001,583 B2 | 8/2011 | Waizumi et al. | |
| 2002/0116512 A1 | 8/2002 | Amit et al. | |
| 2003/0177112 A1 * | 9/2003 | Gardner | 707/3 |
| 2003/0182304 A1 | 9/2003 | Summerlin et al. | |
| 2003/0216919 A1 | 11/2003 | Roushar | |
| 2004/0054521 A1 | 3/2004 | Liu | |
| 2004/0098472 A1 | 5/2004 | Styles et al. | |
| 2005/0021740 A1 | 1/2005 | Bar et al. | |
| 2006/0218115 A1 | 9/2006 | Goodman et al. | |
| 2008/0147854 A1 | 6/2008 | Van Datta et al. | |
| 2009/0019538 A1 | 1/2009 | Pandya | |
| 2009/0168651 A1 | 7/2009 | Xie | |
| 2009/0187968 A1 | 7/2009 | Roese et al. | |
| 2010/0287615 A1 | 11/2010 | Martin et al. | |

OTHER PUBLICATIONS

Spiros Ioannou , Loic Kessous , George Caridakis , Kostas Karpouzis , Vered Aharonson , Stefanos Kollias. "Adaptive On-Line Neural Network Retraining for Real Life Multimodal Emotion Recognition". Lecture Notes in Computer Science, Publisher Springer Berlin / Heidelberg, ISSN 0302-9743, vol. 4131, ISBN 978-3-540-38625-4, 2006. URL: http://citeseerx.ist.psu.edu/viewdoc/summary?doi=10.1.1.107.9500.

* cited by examiner

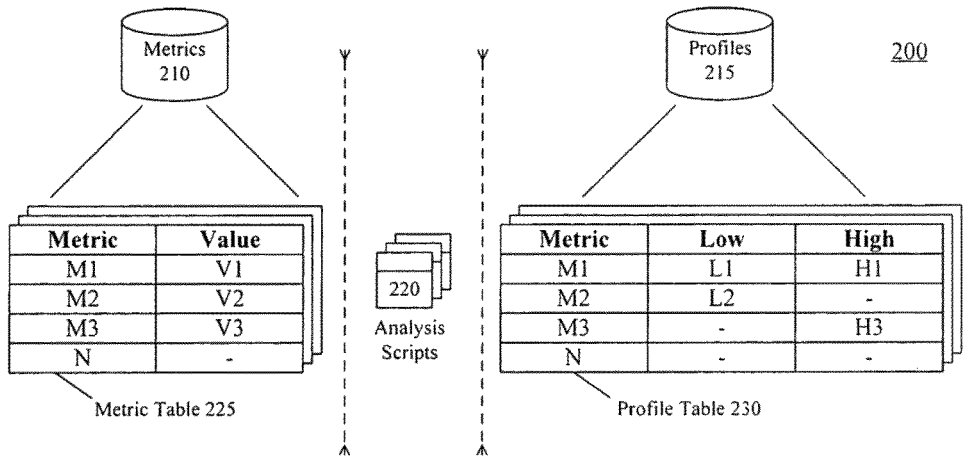

FIG 2A

| Factor | Predominance | Information Source | Condition |
|---|---|---|---|
| Port1214 | High(8) | srvcRawSocket | UDP:dest_port==1214 |
| GetString | High(8) | appSnort | Contains: "get = /." |
| Point2MP | Absolute(10) | srvcRawSocket | Behavior: src_ip[Unique;-1,interval]->dst_ip [Unique;1-12,count;30,interval] |
| DNSqueries | Medium(5) | appDNSCache | Behavior: src_ip[Unique; 30;interval]->query_type [A,type;1,commonality] |

| Factor | Predominance | Information Source | Condition |
|---|---|---|---|
| BadHTTP | High(8) | appSnort | Contains:"get HTTP/1.1_0d 0a 0d 0a_" |
| BadHTTP | High(8) | appApacheLogHost144 | Contains:"client sent HTTP/1.1 request without hostname" |
| BadHTTP | High(8) | appApacheLogHost144 | Contains:"mod_ssl: SSL handshake inerrupted by system" |
| BadHTTP | Absolute(10) | BadHttp:1,2 | Time: 1,interval |
| Chkrootkit | Absolute(10) | appChkrootkit | Contains:"Warning: Possible Slapper Worm installed" |

SYSTEM, METHOD AND APPARATUS FOR CLASSIFYING DIGITAL DATA

This application is a continuation in part of application Ser. No. 10/852,776, published as 2006/0031463 on Feb. 9, 2006, and also claims priority to applications 61/432,795 filed on Jan. 14, 2011; 61/489,535 filed May 24, 2011; and 61/567,408, filed on Dec. 6, 2011. Each of applications 10/852,776, 61/432,795, 61/489,535, and 61/567,408 are hereby incorporated herein by reference in their entireties.

BACKGROUND

The present invention relates to the field of systems, methods, and apparatuses for classifying input data through application of an evolving network in which groupings within the network correspond to commonalities in the input data. The systems, methods and apparatuses of the present invention are applicable in a variety of areas including network management and intrusion detection, identification of patterns in large databases and files, classifying portions of strands of DNA, identifying patterns in graphs, and classifying particular types of network traffic based on common properties or characteristics.

Adaptive classification systems, including systems based on neural networks and self organizing maps are known in the art, and have been applied to solve problems including network management and network intrusion detection. Such solutions, however, have largely required (i) normalization of the input data into numeric vectors based on predetermined selections of parameters thought to be relevant to a particular problem, or indicative of a particular characteristic, and center point calculations based on the normalized values, or (ii) pre-training of a neural network or similar system based on a known data set thought to be similar to the data set to be analyzed. Both sets of solutions have difficulty adapting to constantly changing data sets (such as network traffic) as, the further the characteristics of the input data move away from those of the training data, the less effective the systems become. Such solutions, including those that require normalization of input data into numeric vectors and computation of center points, also impose computational overhead and a predetermined organization on the input data by virtue of the normalization process. This further compromises the solutions' ability to adapt to new, previously unseen patterns and creates computational overhead that makes the systems unusable in applications like network analysis, in which large volumes of data must be analyzed in real-time. In such applications, storing the data set for later analysis is impractical, both because of the size of the data set involved and because of the need for real time identification of anomalies.

The present invention improves on such systems by utilizing a neural foam that classifies nodes without the need for pre-training. Embodiments of the present invention are also capable of classifying data based on an information distance without normalizing the input data into a numeric N-tuple. This results in a more flexible system that classifies input data in its raw form, thereby making it adaptable to a broader range of applications. It also eliminates the need to maintain an evolving center point, which assists in obtaining greater computational efficiency. Embodiments according to the present invention, including those based on information distance, are adapted to systems in which streams of data must be analyzed in real time, and continuous learning over time is required such that new patterns can be identified more quickly than is typically possible with systems that require pre-training or pre-selection of characteristics that are thought likely to be relevant to a particular problem.

As is discussed above, the present invention is adapted to a variety of applications, including network management and intrusion detection. Prior to the present invention, network management was typically handled in a modular fashion, where a software component or hardware device handled a designated operation. For example, network traffic is typically handled by routers, bridges, and hubs; firewalling is commonly handled by a software application; data access restrictions are commonly handled by a file managing component of an operating system; and e-mail filtering can be handled by an e-mail server routine. These modular network management tools usually utilize locally available information in their operation, where enforced policies are typically based upon one or more parameters relating to a request.

For example, file management systems usually require a data requesting source to identify itself by computer identifier and/or user identifier. The file management system then bases access rights upon the user identification and/or computer identifier. In another example, an e-mail filtering program can analyze e-mail parameters and only deliver e-mail that passes previously established criteria. That is, e-mail can be denied if it comes from a suspect sending source if content contains key words or graphics that indicate that the e-mail is an unsolicited advertisement and if the e-mail message fails to satisfy virus and malicious program detection algorithms.

Another conventional network management methodology relies upon establishing a fixed communication protocol relating to a particular function, where operational decisions can be dependent upon conditions established by the protocol. For example, the simple network management protocol (SNMP) establishes a standard for gathering statistical data about network traffic and the behavior of network components. SNMP defines communication devices as either agents or managers, where an agent provides networking information to a manager application running on a different computer. Similar message protocols and enterprise management protocols exist that define a standard and require external devices to adhere to that standard before operations are permitted.

Unfortunately, policies established by such network management solutions can be foiled easily. More specifically, traditional network management systems can be compromised by outside sources that have knowledge of low-level specifics relating to a system. That is, most complex systems have a number of discernable weak points (sometimes called exploits) that can be used to circumvent network policies that administrators attempt to implement. It is practically impossible to design network equipment that does not have some exploitable weaknesses. As soon as one weakness is patched, two or more new weaknesses are discovered and are available to be exploited. Further, each new hardwire device, operating system, network protocol, and technology introduces its own new weaknesses.

Conventional network management solutions have thus failed to approach network management from a holistic perspective. A holistic approach would permit the decoupling of network policies from modularly defined protocols, devices, and software applications. Accordingly, data synergy achieved when combining network data from available network components has not been leveraged to enact network policies that cannot be easily circumvented. Such systems are thus well suited to embodiments of the present invention, as such embodiments provide a holistic, incrementally-learning data classification system that does not require pre-training and are capable of real-time, or near-real-time, analysis of network traffic, and can do so holistically.

SUMMARY

The present invention provides incrementally-learning methods, systems and apparatuses for classifying data, typically in large data sets. More specifically, in the methods, systems and apparatuses described herein, data elements are compared against a set of stored, representative data elements based on a threshold value. Where a distance between the stored, representative data elements and the input data element is less than a threshold value, the input data element is associated with the representative data element. Where such distance is not less than the threshold value, the input element is stored as a new representative data element. Associations can be output to represent the categorizations of input data elements and representative data elements based on common properties. In certain embodiments, further associations are made between new data elements and at least one closest representative data element, as determined based on the distance calculation.

One aspect of the present invention can include an incrementally-learning data classification system. The system can comprise at least one specially-programmed server having a processor and at least one machine-readable storage. The specially-programmed server is connected to a network and adapted to receive input data elements from that network. In certain embodiments, the server is specially programmed to compute a compression distance between the input data elements and a plurality of stored representative data elements. In other embodiments, the server is specially programmed to (i) compute a plurality of metrics for the input data elements, (ii) form those metrics into a vector, and (iii) compute a Cartesian or Manhattan distance between such vector and corresponding vectors for a plurality of stored representative data elements. Where the computed distance is less than a threshold value, the input data element is associated with the representative data element and the processor of the server executes a predetermined set of instructions. Where the computed distance is not less than the threshold value, the input data element is stored as a new representative data element. The server is further adapted to output the associations, whereby the input data elements are classified.

A further aspect of the present invention can include an incrementally-learning data processing system for classifying data. The system can comprise at least one computer processor means for processing data, such means being operably connected to a network. The system can further comprise at least one storage means for storing data available for processing by at least one processor, and at least one first means for receiving input data elements from the computer network, and at least one second means for computing a distance between such input data elements and a plurality of representative data elements stored in the storages means. In certain embodiments, a compression distance is computed between the input data elements and a plurality of stored representative data elements. In other embodiments, (i) a plurality of metrics is computed for the input data elements, (ii) those metrics are formed into a vector, and (iii) a Cartesian or Manhattan distance is computed between such vector and corresponding vectors, for a plurality of stored representative data elements. Where the computed distance is less than a threshold value, the input data element may be associated with the representative data element, and a predetermined set of instructions is executed, thereby classifying the input data element with the corresponding representative data element. Where the computed distance is not less than the threshold value, the input data element is stored as a new representative data element.

A further aspect of the present invention can include a method of classifying traffic on a network involving using at least one specially-programmed server comprising a processor and at least one machine-readable storage medium. The method can include the steps of providing at least one specially-programmed server having at least one machine-readable storage and being operably connected to the network. Further steps comprise causing the server to receive input data elements from network traffic on the network. In certain embodiments, the server is specially programmed to compute a compression distance between the input data elements and a plurality of stored representative data elements. In other embodiments, the server is specially programmed to (i) compute a plurality of metrics for the input data elements, (ii) form those metrics into a vector, and (iii) compute a Cartesian or Manhattan distance between such vector and corresponding vectors for a plurality of stored representative data elements. Where the computed distance is less than a threshold value, the input data element is associated with the representative data element. Where the computed distance is not less than the threshold value, the input data element is stored as a new representative data element. The server is further adapted to output the associations, whereby the input data elements are classified.

A still further aspect of the present invention can include a machine-readable storage medium. The medium contains instructions to cause a specially-programmed server, which is operably connected to a computer network, to perform a method of classifying traffic on that network. The method can include the steps of receiving input data elements from network traffic on that network. In certain embodiments, a compression distance between the input data elements and a plurality of stored representative data elements is computed. In other embodiments, a plurality of metrics for the input data elements are computed and formed into a vector. A Cartesian or Manhattan distance is then computed between such vector and corresponding vectors for a plurality of stored representative data elements. Where the computed distance is less than a threshold value, the input data element is associated with the representative data element. Where the computed distance is not less than the threshold value, the input data element is stored as a new representative data element. Associations are output, whereby the input data elements are classified based on common properties or characteristics.

BRIEF DESCRIPTION OF THE DRAWINGS

There are shown in the drawings embodiments that are presently preferred, it being understood, however, that the invention is not limited to the precise arrangements and instrumentalities illustrated.

FIG. 2A is a schematic diagram illustrating a system that compares network space metrics against factors of a profile in accordance with the inventive arrangements disclosed herein.

FIG. 2B illustrates a table for a peer-to-peer profile in accordance with the inventive arrangements disclosed herein.

FIG. 2C illustrates a table for a worm detection profile in accordance with the inventive arrangements disclosed herein.

DETAILED DESCRIPTION

Figure 1:
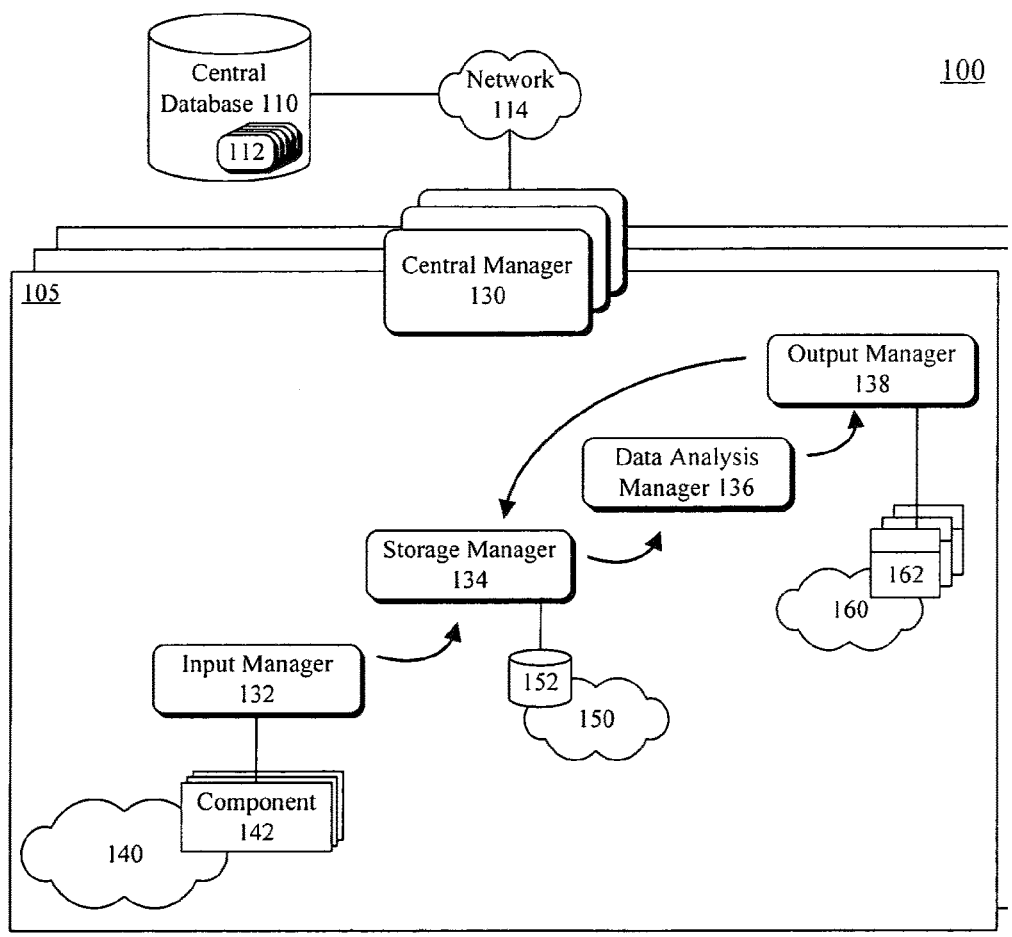
FIG. 1 is a schematic diagram illustrating a system that utilizes a holistic metric driven approach for managing networks in accordance with the inventive arrangements disclosed herein.

Following is a description of preferred embodiments of the systems, methods, and apparatuses according to the present invention. It will be understood by those of ordinary skill in the art that the embodiments described herein are representative of the present invention and are not limitative thereof as other variations and implementations will be apparent to those of ordinary skill of the art based on the following disclosure.

Herein, the following terms are intended have the indicated meanings:

The term "adapted" shall mean programmed, connected, arranged, sized and otherwise configured.

The term "data element" shall mean a set of binary data containing a unit of information. Examples of data elements include, without limitation, a packet of data flowing across a network; a row returned from a database query; a line in a digital file such as a text file, document file, or log file; an email message; a message system message; a text message; a binary large object; a digitally stored file; an object capable of storage in an object-oriented database; and an image file, music file, or video file. Data elements often, but do not always, represent physical objects such as sections of a DNA molecule, a physical document, or any other binary representation of a real world object.

The term "instructions" shall mean a set of digital data containing steps to be performed by a computing device. Examples of "instructions" include, without limitation, a computer program, macro, or remote procedure call that is executed when an event occurs (such as detection of an input data element that has a high probability of falling within a particular category). For the purposes of this disclosure, "instructions" can include an indication that no operation is to take place, which can be useful when an event that is expected, and has a high likelihood of being harmless, has been detected, as it indicates that such event can be ignored. In certain preferred embodiments, "instructions" may implement state machines.

The term "machine readable storage" shall mean a medium containing random access or read-only memory that is adapted to be read from and/or written to by a computing device having a processor. Examples of machine readable storage shall include, without limitation, random access memory in a computer; random access memory or read only memory in a network device such as a router switch, gateway, network storage device, network security device, or other network device; a CD or DVD formatted to be readable by a hardware device; a thumb drive or memory card formatted to be readable by a hardware device; a computer hard drive; a tape adapted to be readable by a computer tape drive; or other media adapted to store data that can be read by a computer having appropriate hardware and software.

The term "network" or "computer network" shall mean an electronic communications network adapted to enable one or more computing devices to communicate by wired or wireless signals. Examples of networks include, but are not limited to, local area networks (LANs), wide area networks (WANs) such as the Internet, wired TCP and similar networks, wireless networks (including without limitation wireless networks conforming to IEEE 802.11 and the Bluetooth standards), and any other combination of hardware, software, and communications capabilities adapted to allow digital communication between computing devices.

The term "operably connected" shall mean connected either directly or indirectly by one or more cable, wired network, or wireless network connections in such a way that the operably connected components are able to communicate digital data from one to another.

The term "output" shall mean to render (or cause to be rendered) to a human-readable display such as a computer or handheld device screen, to write to (or cause to be written to) a digital file or database, to print (or cause to be printed), or to otherwise generate (or cause to be generated) a copy of information in a non-transient form. The term "output" shall include creation and storage of digital, visual and sound-based representations of information.

The term "server" shall mean a computing device adapted to be operably connected to a network such that it can receive and/or send data to other devices operably connected to the same network, or service requests from such devices. A server has at least one processor and at least one machine-readable storage media operably connected to that processor, such that the processor can read data from that machine-readable storage.

The term "system" shall mean a plurality of components adapted and arranged as indicated.

The meanings and definitions of other terms used herein shall be apparent to those of ordinary skill in the art based upon the following disclosure.

It will be understood that the systems, methods, and apparatuses of the present invention may be used in a variety of applications in which it is necessary to classify data elements in a large data set. Examples include, but are not limited to, identifying patterns and anomalies in digital files, database tables, in files representing complex graphs (including without limitation large GraphML files) and within streams of digital data including, without limitation, traffic on a network. Certain preferred embodiments include, by way of example, a network management system.

FIG. 1 is a schematic diagram illustrating a system 100 that utilizes a holistic metric-driven approach for managing networks in accordance with the inventive arrangements disclosed herein. The system 100 can include a central database 110 located in a computing space external to at least one defined network space 105. The central database 110 can centrally contain data utilizable by several different network spaces 105 for policy establishment and enforcement purposes. Administrators can modify data in the central database 110, which can be responsively propagated to all suitable network elements regardless of the network space 110 with which the elements are associated.

The central database 105 can be managed through a database management application, where the database management application is an application external to other components of system 100. The invention is not limited in this regard, however, and software managing the central database 105 can be embedded within other components of system 100.

In one embodiment, the central database 110 can define one or more profiles indicative of a targeted network activity. A profile can be based upon multi-factored metrics. For example, a profile can exist defining peer-to-peer networking activity, worm activity, network intrusion activities, network problem activities, and the like. Stored network profiles can be generic profiles, can be network space 105 specific, and can contain a combination of generic and network-space-specific factors.

In another embodiment, the central database 110 can contain a multitude of model software kernels 112, where a software kernel 112 can be an event-driven state machine responsible for a network management operation. One or more model kernel 112 can exist for each functional kernel type. Functional types of kernels can include, but are not limited to, an input manager 132, a storage manager 134, a data analysis manager 136, an output manager 138, and a central manager 130. Changes made to one of the model kernels 112 can result in corresponding changes being made to all software kernels of a functional type. [46] In such embodiments, the systems, methods, and apparatuses of the present invention can be pre-loaded with sets of representative data elements. As is described further below, however, pre-loading a set of representative data elements is not necessarily equivalent to pre-training a neural network or similar learning system as such pre-loaded data need not be treated any differently than new data that is classified by the system, method or apparatus over time. In this way, embodiments of the systems, methods and apparatuses of the present invention can be seen as learning incrementally, with each new input data element potentially adding to or refining the set of representative data elements previously stored.

Continuing with the network management example, the input manager 132 can gather network metrics, for example, from at least one network component 142. Multiple input manager kernels 132 can exist within the network space 105, each associated with a sub-network 140 of the network space 105. The sub-network 140 can include one or more computing machines, one or more software applications, one or more hardware devices, or portions thereof. In one arrangement, the input manager 132 can be embedded within the component 142, which can conveniently be a hardware device or software routine from which the input managing kernel 132 receives metrics. In another arrangement, the input manager 132 can be externally located from the component 142.

Additionally, the input manager 132 can actively fetch metrics from one or more component 142. The input manager 132 can alternatively passively receive metrics conveyed to it from the components 142 or the network itself. The input manager 132 can also convert data metrics from a format specific to the component 142 into a component-independent format. Moreover, the input manager 132 can include a data cache, where metrics can be temporarily stored before being conveyed to the storage manager 134.

The storage manager 134 can store metrics and/or network management data within memory store 152. The memory store 152 can store data within a single hardware device as well as within a logical memory space spread across multiple devices within a storage network 150. Moreover, memory store 152 can include persistent memory areas as well as temporary memory areas.

In one embodiment, the storage manager 134 can store metrics from the input manager 132 in a global memory cache accessible by the data analysis manager 136. The storage manager 134 can store data within a file structure system as well as within a database structure. The storage manager 134 can define storage specific interfaces for each storage type it uses, thereby allowing the storage manager 134 to be implemented in a database-independent and/or file-system-independent manner. Further, the storage manager 134 can automatically delete or archive metrics after a designated period. Storage manager 134 can also store data within a distributed database in which data is spread across multiple devices within a storage network 150, but may be stored and accessed as if it is within a logical memory space.

Storage manager 134 can contain copies of the data elements to be analyzed. In this way it will be understood that storage manager 134 stores representative data elements stored in a machine-readable storage in storage network 150. As is discussed further below, where the embodiment utilizes a compression distance calculation, the stored representative data elements will preferably comprise copies of the data elements themselves. Where the embodiment utilizes a Cartesian distance or Manhattan distance, it may be preferable to also store a plurality of metrics calculated from the input data element in addition to, or instead of, the representative data elements themselves.

The data analysis manager 136 can analyze data received from the input manager 132 and storage manage 134 in real time, or can analyze data stored by storage manager 134. The data analysis manager 136 can use a profile of multiple factors, each of which can be compared against corresponding metrics. Stronger correlations can result in stronger confidence levels that the network event or usage has occurred. The data analysis manager 136 can trigger one or more event operations depending upon the correlation between the footprint and the profile.

The data analysis manager 136 can utilize any of a variety of techniques to perform the correlation including algorithmic and heuristic techniques, pattern matching and topological techniques, supervised and unsupervised techniques, fuzzy logic and probabilistic techniques, and the like. In one embodiment, the data analysis manager 136 can include a neural network and/or an expert system that analyze network metrics according to trained criteria. For example, a neural network refined by genetic algorithms can be used to locate patterns within collected data of an information space. The invention is not limited in this regard, however, and any correlation technique can be used by the data analysis manager 136.

The data analysis manager 136 can analyze metrics using small samples of the metrics and/or can utilize large metric samples as appropriate. Additionally, administrator selectable and/or multiple statistical analysis techniques can be utilized by the data analysis manager 136. The data analysis manager 136 can also devote different levels of resources to different profiles.

In one embodiment, a profile representing a critical network policy can be analyzed more often and more exhaustively than a profile representing a minor network policy. In such an embodiment, an analysis of critical network policies can occur in near-real time and an analysis of minor network policies can occur on a daily, weekly, or monthly basis. In another embodiment, the data analysis manager 136 can receive metrics, such as metrics associated with single factor actions, directly from the input manager 132 for expedited processing.

One particularly useful means of data analysis is described herein (and in the incorporated references) as "neural foam." As disclosed herein, neural foam may be built in two basic forms: compression-distance foam or Cartesian/Manhattan-distance foam.

A Cartesian/Manhattan-distance foam comprises multi-dimensional vectors. Input manager 132 may calculate such vectors from input data elements as a plurality of metrics. As used herein, the term metric refers to a value that can be calculated from the input data element. Examples for embodiments in which input data elements represent packets of network data could include, without limitation, the source or destination addresses of the network data, the size of the network packet, a hash of the network packet, a value representing the similarity between the network packet and a profile network packet, or any variety of other values that can be readily computed from the network packet itself. For embodiments in which input data elements represent message system messages, examples of metrics could include, without limitation, message sender or recipient, message size, a dictionary of specific terms within the message, a hash of the message, a value representing the frequency of occurrence of a predetermined set of strings within the message, or, again, any value that can be readily computed from the message itself or its encoded address and delivery information. Similarly, examples of metrics for embodiments in which input data elements represent rows returned from a database table or query could include, without limitation, the row size, any subset or value within the row, the result of applying a computational formula to the entire row or some element, or set of elements within the row, or, again, any value that can readily be computed from the row. As can be seen from the foregoing, certain similar metrics can be derived from different types of input data elements whereas other metrics are unique to a particular type of input data element. A variety of appropriate metrics for different embodiments and different types of input data elements will be apparent to those of skill in the art in light of the foregoing.

The method or process of building the neural foam starts with two representative vectors, or neural nodes (in embodiments of systems, methods and apparatuses according to the present invention that utilize neural foam for data analysis, a node is also a representative data element). Each time an input vector is fed into the network, a new node is inserted in its location if it comes from an unidentified region. For our purposes here, an unidentified region is one such that the distance from the input to its closest two neighbors is greater than either of their similarity thresholds, where a similarity threshold is a value based on the distance (as is described further below) between the nodes. Otherwise, if the input vector lies within the similarity thresholds of its two closest neighbors, then the weight vectors of the winner and second winner (nearest and next-nearest neighbors) are adaptively adjusted. Subsequently, the winner and second winner are connected if they were not previously connected.

Basing the node insertion strategy upon a similarity threshold allows the system to carry a sense of perspective on the size of the area in the input space that each node represents based on the input data elements encountered to date. The smaller the similarity threshold the more discriminating the system will become within that region of the input space.

Periodically nodes in the foam are checked with two purposes in mind: 1) ensuring cluster consistency based on a similarity threshold and 2) the culling of nodes with both low relative signal count and low connectivity to other nodes. To accomplish the first purpose, connections are added between pairs of unconnected nodes wherever one of the nodes falls within the similarity threshold of the other, while at the same time removing connections between nodes where their distance from one another exceeds the threshold of either node (favoring the newly added connection in the case where both conditions hold in sequence). After this is completed, the nodes that are not well connected, as defined by having at most one topological neighbor and have a signal count below a fraction of the average signal count, are removed.

The system thus adopts an adaptive learning rate scheme so that each node has it own learning rate. At each iteration, as vectors are fed into the foam, the signal count of the winner is incremented, should the input vector lie within the winner's similarity threshold. The individual learning rate is defined by a function that satisfies the Robbins-Monro Algorithm requirements, namely that the function is not summable, yet it is square summable. One appropriate such function is the inverse of the signal count. This scheme allows the network to vary its adjustment of nodes based on the amount of data each node is representing in the network. Notably, this is different from self organizing maps (SOMs), Growing Neural Gas (GNG) and Growing Cell Structure (GCS) networks, which typically use a Gaussian, global, learning rate, and are otherwise not well suited for incrementally learning data element classification systems, methods, and apparatuses that typically have to analyze large, potentially evolving data sets without the benefit of pre-training.

In systems, methods and apparatuses according to the present invention, and unlike systems, methods and apparatuses that utilize GNG-based analysis methods, new nodes are not inserted in a fixed interval manner. Over a long time, having a fixed insertion rate policy is not advantageous since it is likely to require the system to make unnecessary or untimely insertions. Unneeded node insertion can result in misclassification problems. In certain embodiments of the system according to the present invention, each node has a sense of prospective similar vectors, which is quantified by its similarity threshold. When an input vector lies within the similarity thresholds of its two nearest nodes it is considered to be already represented by them. However, should it lie outside either threshold, then it is something that is not sufficiently well known to the system and thus merits its own representative node. Because the new node is effectively unknown it is initiated with a high (infinite) similarity threshold. As new input vectors occur close to this new node (i.e., it is the winner or second winner) the system gains an increasing knowledge of what the node represents, which is reflected by adjusting its similarity threshold, as well as possibly adding connections to other nodes.

In the process applied by a preferred embodiment of the system of the present invention, the weight vector is interpreted as the position of a node in the input space. The difference between their respective reference vectors can be seen as the "distance" between the nodes in an N-dimensional space. Calculating distance can be performed using a Cartesian distance (which is synonymous herein with the term Euclidean distance) formula. Calculating a Cartesian distance is somewhat expensive computationally, however.

Accordingly, in embodiments in which computational efficiency is an important factor, the simpler and more computationally-efficient Manhattan distance (sometimes called the taxicab distance) can be used instead.

The following notation is used in the following formalized description of a preferred embodiment of Cartesian/Manhattan-distance neural foam that is appropriate for embodiments of systems, methods and apparatuses according to the present invention:

$W_i$ the n-dimensional weight vector in $R^n$ for a given node i.

$M_i$ local accumulated number of signals attributed to node i, referred to at times as the signal count. It is the number of times node i is the winner (closest node to the current input vector).

$T_i$ similarity threshold for node i. It determines the area around $w_i$ that node i represents currently. If the distance between an input pattern and node i's weight vector is larger than its threshold, $T_i$, the input pattern is a new node.

$L_i$ number of topological neighbors of node i. (number nodes connected to i. by an edge)

$N_i$ set of direct topological neighbors for node i.

$C_k$ cluster label. A cluster is the connected component of nodes, ordered at random.

Other global variables of the Neural Foam algorithm include:

A node set, used to store nodes $N_A$ number of nodes in A

C connection set (or edge set), used to store pair-wise connections (edges) between nodes Q number of clusters (connected components of nodes).

For better understanding, the complete implementation of a vector-based neural foam is summarized in Table 1.

TABLE 1

| | |
|---|---|
| 0. | Identify user decision parameters (including λ, c, and $T_{min}$) |
| 1. | Create an initial node set which contains two nodes $c_1$ and $c_2$ with weight vectors chosen randomly from the input data set: $A = \{c_1, c_2\}$. Thresholds for these nodes need not be initialized (as they will be updated before being used). |
| 2. | Take an input vector $\hat{i} \in R^n$. |
| 3. | Determine the winner (node with the closest weight vector to the input) $s_1$ and the second winner (second-nearest) $s_2$: $s_1 = \arg\min_{j \in A} \|\hat{i} - w_j\|, s_2 = \arg\min_{j \in A\{s_1\}} \|\hat{i} - w_j\|$ |
| 4. | Update the similarity thresholds $T_{s_1}$ and $T_{s_2}$ for the winner $s_1$, and the second winner $s_2$ using the algorithm given below (Table 2). |
| 5. | If the respective distances between i and $s_1$ or $s_2$ are greater than either of the similarity thresholds $T_{s_1}$ and $T_{s_2}$, the input vector is a new node r added to A with weight vector i and similarity threshold of $+\infty$. I.e. if $(\|\hat{i} - w_{s_1}\| > T_{s_1} \| \|\hat{i} - w_{s_2}\| > T_{s_2})$, then $A = A \cup \{r\}$ where $w_r = \hat{i}$; go to step 9 otherwise proceed to step 6. |
| 6. | If a connection between $s_1$ and $s_2$ does not already exist, create it: $C = C \cup \{(s_1, s_2)\}$. |
| 7. | Increment the local signal count of the winner: $M_{s_1} = M_{s_1} + 1$ |
| 8. | Adapt the reference vectors of the winner and the second winner using adaptive learning rate scheme: $\Delta w_{s_1} = \frac{1}{M_{s_1}}(\hat{i} - w_{s_1}), \Delta w_j = \frac{1}{100 * M_j}(\hat{i} - w_j)(\forall j \in N_{s_1})$. |
| 9. | If the current iteration is an integer multiple of parameter λ, update the topological neighborhood of each node and remove the nodes in low probability density. Connect each node to all nodes located within its similarity threshold and disconnect its connection from any node if |

TABLE 1-continued

| | |
|---|---|
| | it located farther from its similarity threshold. If for any pair of nodes one node is within its partners' similarity threshold, but the other one is not, connection has priority over disconnection. Remove the nodes without a neighbor or having only one neighbor and having a signal count less than a fraction of the average signal count I.e. if $((L_i = 0 \text{ or } L_i = 1)$ and $M_i < c \sum_{j=1}^{N_A} M_j / N_A)$, then $A = A \setminus \{i\}(\forall i \in A)$. |
| 10. | Got to step 2 for a new input vector. |

The process for calculating the similarity threshold of the nodes is presented in Table 2.

TABLE 2

| | |
|---|---|
| 1. | The default of the similarity threshold for a new node is $+\infty$ (no knowledge). |
| 2. | Every time a node i is either the winner or second winner, update its similarity threshold $T_i$ by |
| 3. | If the node has direct topological neighbors ($L_i > 0$), $T_i$ is the maximum distance from node i to its topological neighbors: $T_i = \max_{j \in N_i} \|w_i - w_j\|$ <br> If the node has no topological neighbors ($L_i = 0$), T, is the minimum distance from node i to the other nodes in A: $T_i = \min_{j \in A\setminus\{i\}} \|w_i - w_j\|$ |
| 4. | Bound the similarity threshold $T_i$ by lower bound $T_{min}$ (i.e. if it is less than $T_{min}$ set it to it). So in other words, the similarity threshold $T_i$ should be greater-than-or-equal-to the pre-specified minimum similarity threshold $T_{min}$. |

In addition to having neural foam comprising multi-dimensional vectors in which distances are based on Cartesian or Manhattan distances, it is also possible, and in certain embodiments is preferable, to have foams comprising uni-dimensional nodes in which distances are based on compression distances or information distances. In an example of one such embodiment, in system 100, input manager 132 need not calculate a plurality of metrics from the input data elements. Instead, the input data element can be treated as or reduced to a single digital value and distances can be calculated by determining the compression distance or information distance between input data elements and representative data elements. Depending on how the reduction is done, however, it is possible to lose fidelity such that a close distance between two reduced values does not necessarily suggest any meaningful commonality between them. Therefore, it is useful to identify specific reduction techniques that can be applied efficiently, treat the input data object to single value, and do so in a way that does not lose too much of the underlying information content.

Data compression is one such technique. As an example of such an embodiment, data analysis manager 136 will compress each input data element using a compressor function and compare the results of the compression to representative data elements stored by storage manager 134 in order to determine a theoretical distance between them.

Normalized Compression Distance (NCD) is a family of functions designed with that purpose in mind. NCD functions take as arguments two objects and evaluate a fixed formula expressed in terms of the compressed versions of these objects, separately and combined. Hence this family of functions is parameterized by a compressor (i.e., a function capable of compressing an arbitrary data object). If x and y are the two objects concerned, and C(x) is the length of the compressed version of x using compressor function C, then a normalized compression distance function can be expressed as follows:

$$NCD(x, y) = \frac{C(x, y) - \min\{C(x), C(y)\}}{\max\{C(x), C(y)\}}$$

In this formula, C(x) is the compressed length of object x, C(y) is the compressed length of object y, and C(xy) is the compressed length of the concatenation of object x with object y. Functions of this class can be used to estimate what is known as Kolmogorov complexity. The Kolmogorov complexity and what is known as the Normalized Information Distance cannot be computed directly; they can only be estimated. An NCD function is therefore defined for any compressor and can be used to generate an estimate of the Normalized Information Distance between any two data objects or, in the case of the present invention, between input data elements and stored representative data elements. As the quality of compression improves, the accuracy of the estimation improves. In this way NCD is a universal, alignment-free distance metric that makes no assumptions about the structure of the contents of the data objects used as inputs. Accordingly, whereas prior art solutions and embodiments relying on multi-dimensional vectors rely on a predetermined hypothesis of what metrics or training data sets will be important in future analysis, embodiments based on NCD formulas assume nothing more than that the quality of compressor function C will be sufficient for the function to provide a reasonable estimate of the Normalized Information Distance between input data elements.

Compressor functions that are commonly known and used are lossless. Lossless data compression is a class of data compression algorithms that allows the exact original data to be reconstructed from the compressed data. The term lossless is in contrast to lossy data compression, which only allows an approximation of the original data to be reconstructed, in exchange for better compression rates. Thus, herein, the term "lossy compression" refers to a compression function that reduces the size of an object in such a way that only an approximation of the original data can be reconstructed.

Lossless data compression is used in many applications. For example, it is used in the ZIP file format and in the Unix tool gzip. It is also often used as a component within lossy data compression technologies (e.g. lossless mid/side joint stereo preprocessing by the LAME MP3 encoder and other lossy audio encoders). Lossless compression is used in cases where it is important that the original and the decompressed data be identical or where deviations from the original data could be problematic. Typical examples are systems and methods of reducing the size of executable programs, text documents and source code. Lossy compression, in contrast, can be used when the need for size reduction outweighs the need to be able to reproduce the input data exactly. For example, a compressed audio file in the MP3 format may experience a loss of fidelity, but still may be perfectly acceptable to listener under ordinary circumstances.

Lossy compression can be seen as a data encoding method that compresses data by discarding (losing) some of it. The procedure aims to minimize the amount of data that need be held, handled, and/or transmitted. Lossy compression is currently only used to compress multimedia data (audio, video, and still images), especially in applications such as streaming media and internet telephony. In such applications, the need for a higher degree of data compression outweighs the cost of a certain loss in fidelity. By contrast, lossless compression is required for text and data files, such as bank records and text articles, where loss of even a small amount of information can render the file unusable. For this reason, there are no examples in the literature of a lossy compressor being used for compression of generic data files such as text, data files, binary files, etc.

As was described above, a lossy compressor is one that discards some of the data which describes its input. Unlike existing lossy compressors for multimedia, which discard data based on human perception of the end result, embodiments of the present invention make use of lossy compressors that discard data that is unnecessary to describe the model (structure) of the input data object. This can be seen as a quantization of the opcodes and/or literals that constitute the input. For example, given the input "1234512345" a lossless compressor might output "12345C(-5)". This indicates 5 literals (1,2,3,4,5) and one copy operation (C(-5)) of offset minus five (meaning copy the previous five characters and insert them here). In contrast, given the input "1234512345" a lossy data compressor might output "1AC". This indicates a starting literal of 1, a numeric ascent (from 1 to an unspecified number), followed by a copy operation (of unspecified length). Reversing this lossy compressor's output might result in many strings, such as "123451", "123453", "12345345", "1212", "1234512345", etc., only one of which matches the input exactly.

Any string decomposition, combinatorial, or other model typically used for lossless compression can be decomposed for use in a lossy generic data compressor by quantizing the opcodes and literals. For example, one might decide to quantize all copy operations by stating that they have a size of "1", while numeric values might be quantized by taking the log base 2 of the value, and dropping the mantissa of the result. Another implementation may quantize all general operations by stating that they have variable sizes dependent on an independent ranking, while numeric values might be quantized by taking the square root of the value and rounding the result to an integer value. While applying lossy data compression to arbitrary binary objects has been seen as having little or no value, the systems and methods of the present invention demonstrate that lossy compression can be used in combination with NCD to create an efficient data classification system.

Figure 6:
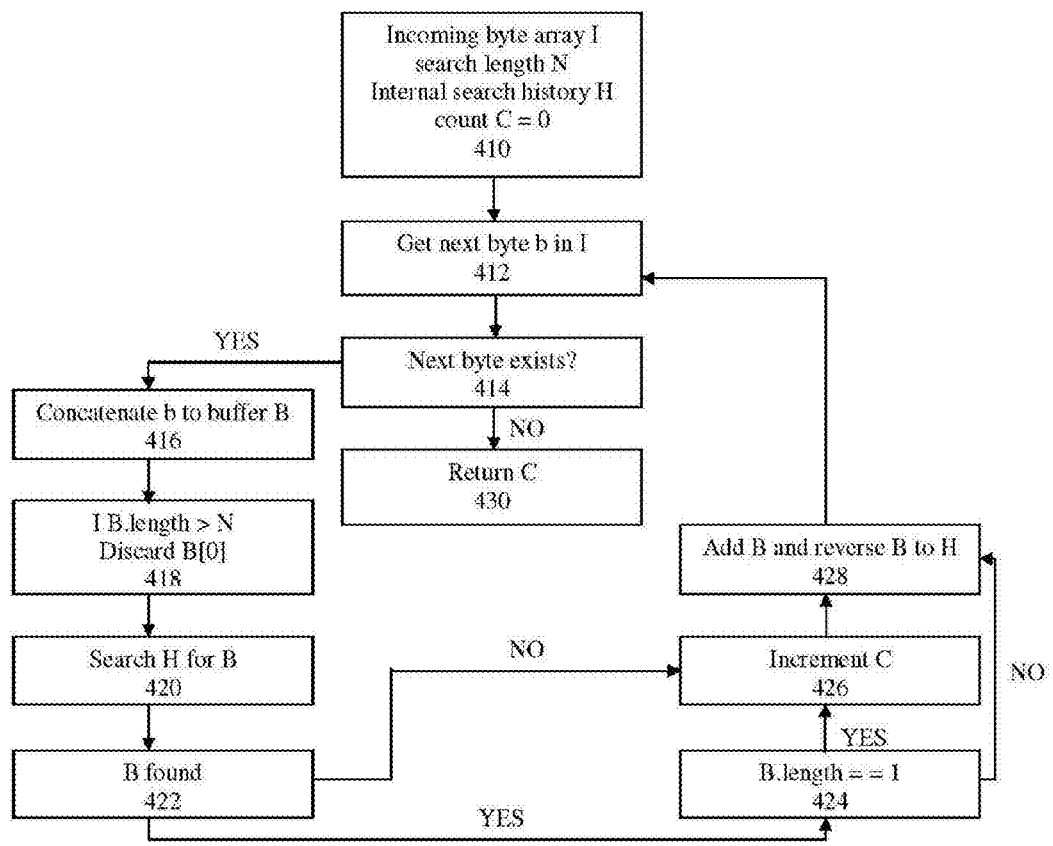
FIG. 6 is a flowchart illustrating steps of a compression calculation suitable for use in connection with computing compression distances in accordance with the inventive arrangements disclosed herein.

One suitable lossy data compression method is referred to herein as the "Snarky" method and, as is illustrated in the flowchart shown in FIG. 6, operates as follows. The input object is a byte array of any length. In steps 410, 412, 414, the input object is scanned one byte at a time, maintaining (i) a buffer of a currently unmatched subsequence B, a history H of previously encountered subsequences up to length N, and a counter C. In step 416, each new byte is concatenated to B. In step 418, if the length of B is greater than N, the first byte of B is discarded. In step 420, H is then searched for an instance of B. In step 422 if an instance of B is found, and B's length is equal to 1 (shown in step 424), C is incremented in step 426. Otherwise C is not incremented. H is then updated with B and the reverse of B in step 428, and the next byte is scanned in step 412. When end of input is reached, step 430 returns the contents of C.

The Snarky method has been found to be computationally efficient, and to result in a meaningful information distance results that are useful in classifying data into groupings and identifying anomalies. The Snarky method is particularly useful when the input data elements are complex.

An extreme form of lossy compressor is a pseudocompressor. A pseudocompressor is an adaptation of a data compressor strictly for the purpose of estimating complexity or calculating various compression distances. Rather than outputting an encoded string, and various overhead data, a pseudocompressor outputs the counts of literals and/or opcodes only, as yielded by the compression algorithm. Its output cannot be decoded to yield the original input, and multiple inputs will have identical output values. For this reason, pseudocompressors are not typically used in practice. Embodiments of the present invention, however, have shown that pseudocompressors can be useful for estimating the Kolmogorov complexity of an input and as a part of estimating the Normalized Information Distance. By eliminating the information required for reversible compression from the compressed object, use of a pseudocompressor can actually achieve more accurate results in estimations of the Normalized Information Distance in certain applications.

There are several differences between using a pseudocompressor instead of a reversible data compressor when calculating a compression distance, including that the pseudocompressor: (i) outputs possibly weighted or otherwise combined sums of counts of opcodes and/or literals only, (ii) does not output data to restore input file names or other overhead data, such as a regular compressor's dictionary, and, (iii) results in significantly more accurate compression distance measurements, especially in instances of very high or very low vector (extremal) similarity.

Figure 7:
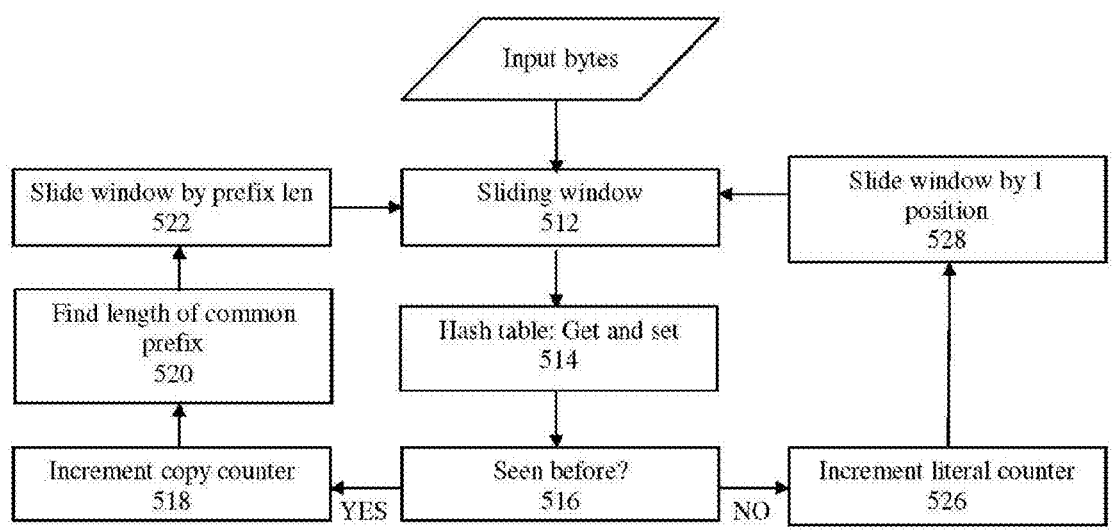
FIG. 7 is a flowchart illustrating steps of a compression calculation suitable for use in connection with computing compression distances in accordance with the inventive arrangements disclosed herein.

While other pseudocompressors may also be used, certain preferred embodiments of the present invention utilize a pseudocompressor method referred to herein as the "Sneaky" pseudocompressor, which is further illustrated in the flowchart shown in FIG. 7. The input to the Sneaky pseudocompressor method is a byte string of any length. The pseudocompressor then operates by scanning a two-byte window over the input string and interpreting the 16 bits at each byte position as an unsigned integer in step 512. A bit-folding or hash function is then applied in step 514 to reduce the 16-bit integer to an N-bit integer, where N is the logarithm (base 2) of the number of slots in an array containing 16-bit offsets (all elements initialized to 0xFFFF). The folded integer is then used to index into the array. At step 516, if the offset at the indexed array slot is 0xFFFF, then increment the "literals" counter at step 526, store into the indexed array slot the current position in the input string, and move the scanning window to the next byte position at step 528. If at step 516 the offset in the indexed array is not 0xFFFF (meaning it has been seen before), then increment the copy counter at step 518 and compare the input string starting at the current position with the input string starting at the stored offset and count the length of the identical substrings at those positions at step 520. Store into the indexed array slot the current position in the input string. The scanning window is then moved to the byte position immediately following the identical substring starting at the current position at step 522. The process stops when the scanning window extends past the end of the input string, and the values of the "literals" counter and the "copies" counter are returned.

The Sneaky pseudocompressor is computationally efficient and works well when using NCD to classify and identify anomalies in large sets of relatively simple data such as lines of text. The NCD method described above, however, makes certain assumptions that limit its usefulness with any reversible compressor. First, it assumes that the compressor is idempotent, meaning, that the compressed length of a string is equal to the compressed length of the string appended to itself. In practice, this is not the case, as the encoding of a copy or other indicative operation takes up some space. This means that under a practical implementation of NCD, no input's distance to another vector will be zero, even if the distance is being measured against itself. Second, NCD assumes that the simplest possible string at any length can be encoded using no characters (zero-length encoding). This is unrealistic with a reversible compressor because at least some characters will be necessary to recover any string.

It is a possible, however to correct for idempotency via a different estimation of the Normalized Information Distance than that of NCD. Following is a revised NCD calculation referred to herein as RLNCD1:

$$RLNCD1(x, y) = \frac{C(xy) - \min\{C(xx), C(yy)\}}{\max\{C(xx), C(yy)\}}$$

RLNCD2 corrects for both idempotency and zero-length encoding via a second different estimation of the Normalized Information Distance. If x and y are the two objects concerned, and C(x) is the length of the compressed version of x using compressor C, and Lxx, Lyy and Lxy are the simplest inputs under the compressor's model at the length of xx, yy and xy, then:

$$RLNCD2(x, y) = \frac{(C(xy) - C(Lxy)) - (\min\{C(xx), C(yy)\} - C(Lxx|Lyy))}{\max\{C(xx), C(yy)\} - C(Lxx|Lyy)}$$

As used herein, the simplest input under a compressor's model at a given length based on the model of the compressor can be thought of as the most compressible input possible for a given input length. For example, in a typical gzip-style compressor, the input "AAAAAAAAAAAAAAAAAAAAAA" (having 22 repetitions of the same character) would be an example of the most compressible input having a length of 22 characters as no other 22 character string would be compressed to a smaller size. Most 22 character strings, such as "Mary had a little lamb" would compress to a larger size. RLNCD2 corrects both mistakes in the original algorithm, and most importantly, produces accurate results when used in neural foam consisting of data elements having lengths less than 100,000.

Figure 4:
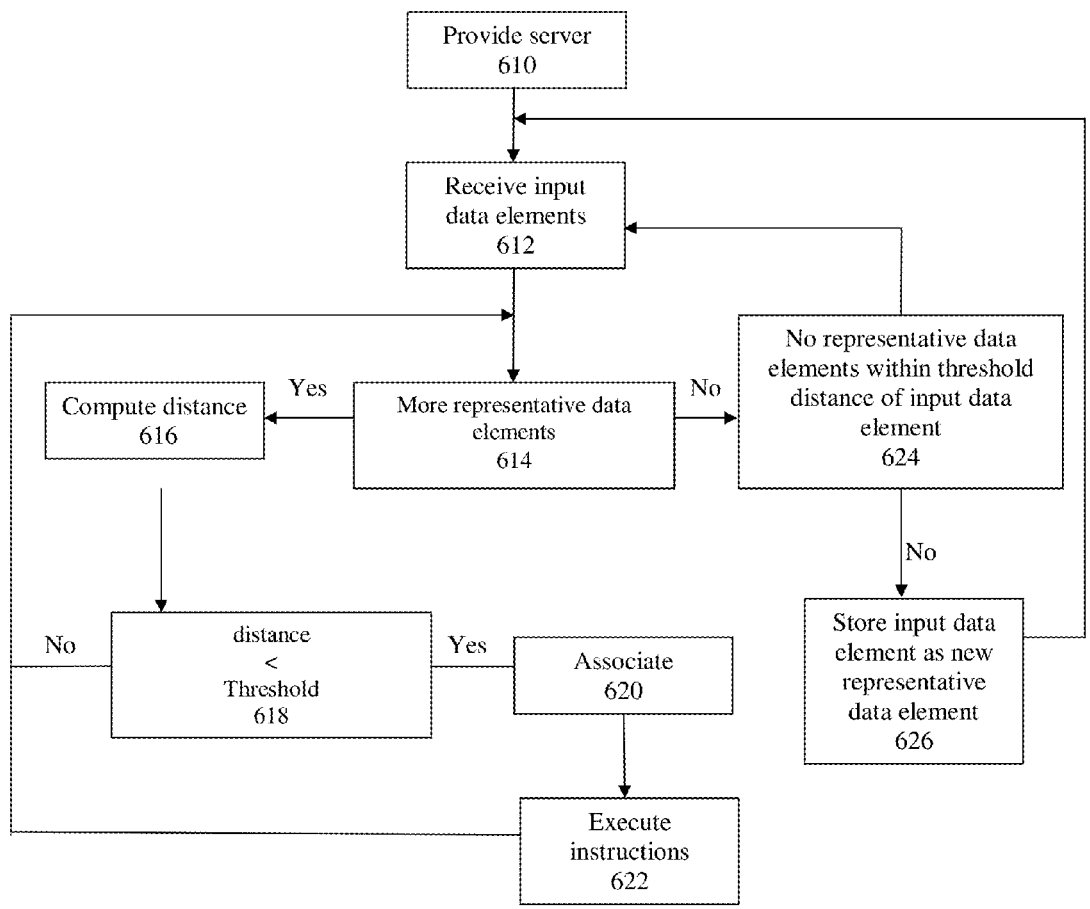
FIG. 4 is a flowchart illustrating steps of an embodiment of a method of classifying data elements in accordance with the inventive arrangements disclosed herein.

It can therefore be seen how an incrementally learning system and method for classifying data elements and identifying anomalies according to the present invention can be constructed. As is illustrated in FIG. 4, at a high level, a specially-programmed server comprising a processor and at least one machine readable-storage is provided at step 610. New input data elements are received, in many embodiments as a stream of data from a network, at step 612. As each new input data element comes in, the compression distance between it and each node in the foam (representative data elements) is calculated in steps 614 and 616. In embodiments in which a neural foam containing multi-dimensional vectors is utilized, distances are calculated as Cartesian or Manhattan distances. In embodiments in which a neural foam comprising uni-dimensional nodes is utilized, distances are calculated as normalized compression distances, preferably utilizing NCD, RLNCD1 or RLNCD2. Where the distance is below a threshold value (step 618), there is a high probability that the input data element can properly be classified as being a member of the same grouping as the representative data element and can, therefore, be associated with that representative data element (step 620). As is described further below, it is often desirable to execute a predetermined set of instructions (step 622) when such an association is identified. Such instructions could perform an appropriate action such as, without limitation, recording the event in a log file or database, alerting a user, updating a display, sending a message, or isolating the input data element. Where the distance is not less than the threshold value, the next representative data element can be tested (step 614). Once all appropriate representative data elements have been tested, it can be determined if any had a distance calculation less than the threshold (step 624). If none did, than the input data element can be stored as a new representative data element (step 626) and the next input data element can be analyzed. As has been described above, when vectors are used in the foam, it is also desirable to create connections between the two closest neighbor nodes as a new node is added, (which would occur subsequent to step 626).

Even given the ability to quickly process input data elements using compression distance or Manhattan distance calculations, analyzing large data sets presents computational challenges, especially where the computation needs to be done in real time or near-real time, such as when analyzing network traffic. To overcome the computational challenge, it is preferred to index the incoming data in a way that allows the classification to be performed quickly such that each input data element need not be tested against every representative data element previously stored.

Figure 8:
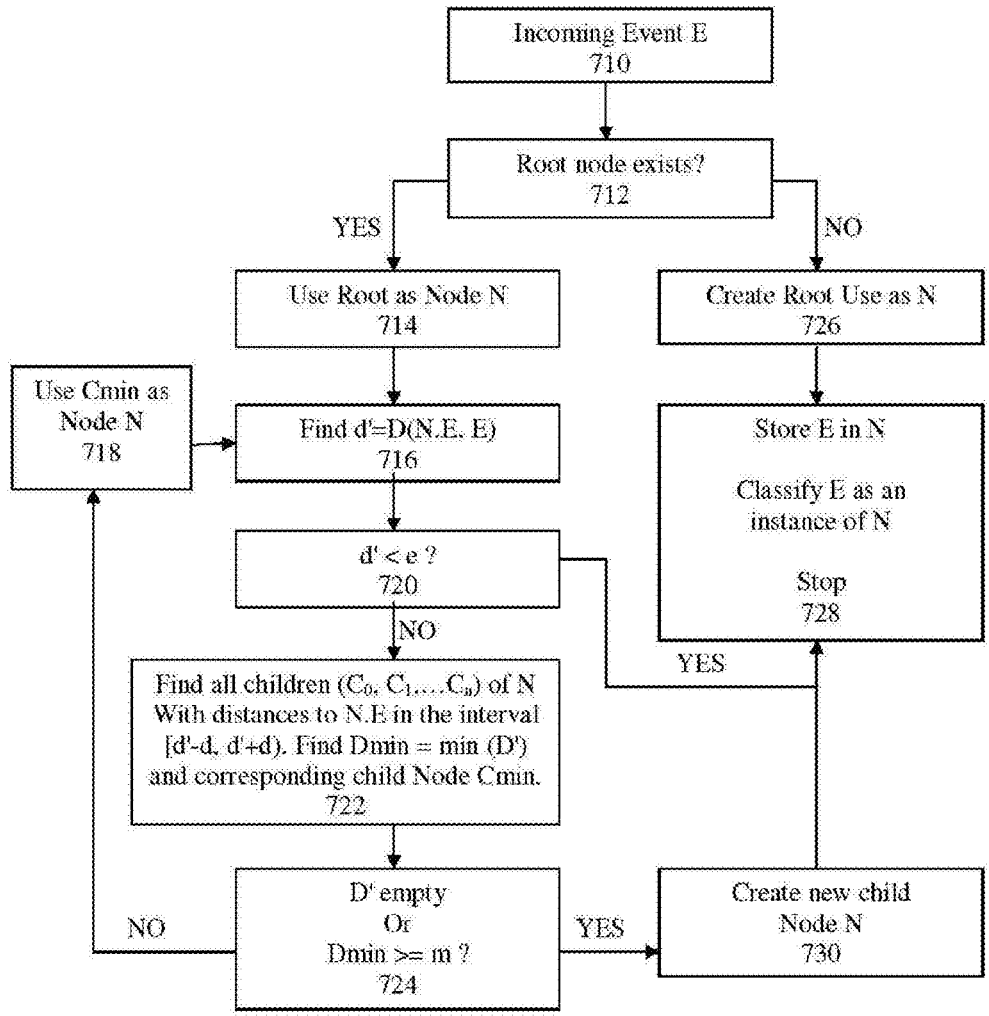
FIG. 8 is a flowchart illustrating steps of a method of utilizing a dispersion tree index of stored representative data elements suitable for use in connection with the inventive arrangements disclosed herein.

A preferred embodiment of the present invention solves this problem with utilizing a novel method referred to herein as a Dispersion Tree, which is preferred when using compression-distance-based neural foams. Instead of comparing each input data element to every representative data element in the neural foam, each input data element is compared only to a subset of previously encountered representative data elements using a tree-based index. As is illustrated in FIG. 8, comparison starts at the tree root node. If there is no root node (step 712) a new root node is created (step 726) and the input data element is stored as a representative data element at the new root node (step 728). Otherwise, at each node of the tree, if the representative data element at the node is close enough to the input data element, the input object is associated with that node (steps 714, 716, 720, 728). Otherwise, find all children of the current node within a dispersion radius of the object's distance to the node's stored value (step 722) and continue classification in the closest node that is below a maximum distance (step 724). If no nodes are found within the dispersion radius then add a new child node to the tree (step 730) and stop. More specifically:

Given event E, Node N Distance function D, dispersion radius d, error tolerance e, and Maximum allowed error m When encountering Event E:
1) If Node N does not exist, create N storing E, classify E as an instance of N, and stop.
2) Otherwise, find d'=D(N.E, E)
3) If d'<e, add E to N.E, classify E as an instance of N, and stop.
4) Otherwise, find all children (C0, C1, Cn) of N with distances to N.E in the interval [d'−d, d'+d) and iterate over those children, finding distances D'=(D(C0_3 E), D(C1, E), . . . , D(Cn, E)). Find Dmin=min(D') and corresponding Cmin.
5) If D' is empty or Dmin>=m (maximum allowed error) then repeat from step 1 with Cmin as Node N.
6) Otherwise, add new child N' to N, store E in N', classify E as an instance of N', and stop.

This effectively populates the Dispersion Tree with new nodes as they come in. Data elements assigned to the same node are classified as having a high probability of belonging to the same grouping. Data elements that are assigned to nodes with only a very small number of other objects can be seen as anomalies.

For efficiency, it is desirable to periodically rebalance the Dispersion Tree. This can be accomplished as follows:
1) Remove the longest branch consisting of only single child nodes from the tree.
2) Reclassify each node in the branch through the tree.
3) Repeat from step 1 until desired tree height reached or no single child branches remain in tree.

Figure 9A:
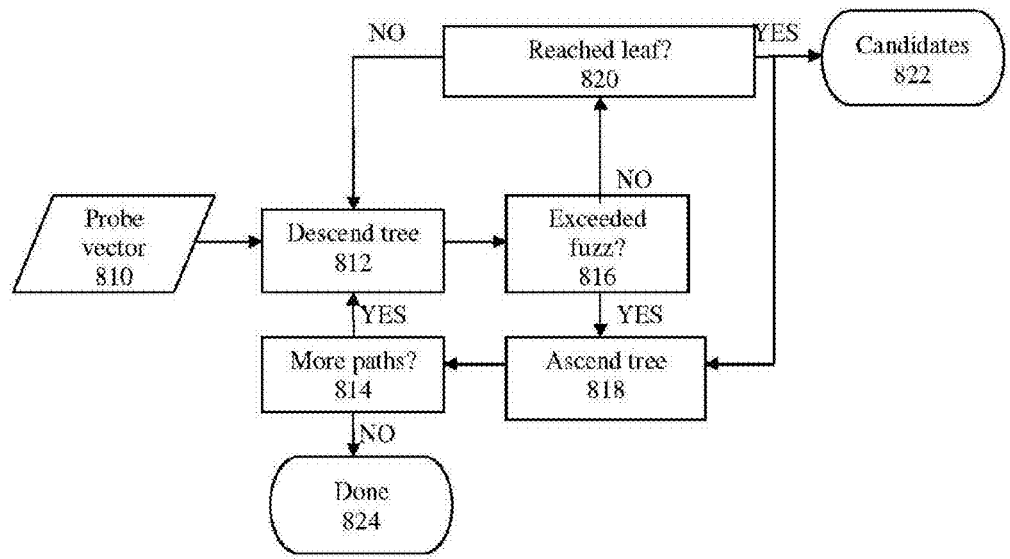
FIG. 9A is a flowchart illustrating steps of a method of utilizing a Charybdis tree index of stored representative data elements suitable for use in connection with the inventive arrangements disclosed herein.

A further preferred embodiment of the present invention solves this problem utilizing a novel method referred to herein as a Charybdis Tree, which is preferred when using Manhattan-distance-based neural foams. Again, instead of comparing each input data element to every representative data element in the neural foam, each input data element is compared to a subset of previously encountered representative data elements using a tree-based index, as is illustrated in FIG. 9A (illustrating a Charybdis Tree search method) and FIG. 9B (illustrating a Charybdis Tree vectorization method).

The Charybdis Tree is a compact prefix tree designed to efficiently index sparse, high-dimensional vectors and to support fast bounded searches. The tree contains three types of nodes: index nodes, count nodes, and leaf nodes. Each index node may have as children any number of count nodes and at most one leaf node. Each count node may have as children any number of index nodes. A leaf node may not have any children. The foregoing implies that the levels of the tree alternate between index levels and count levels, with leaf nodes appearing only on count levels. The root node is an index node.

To encode a vector into the tree, the vector is interpreted as an alternating sequence of indices and counts, where each index is the offset of a position in the vector at which a non-zero element resides and the accompanying count is the value of that element. The vector is scanned for non-zero elements sequentially from the least index to the greatest index. Each index in the produced sequence is used as the key of a count node (which is a child of an index node), and each count in the produced sequence is used as the key of an index node (which is a child of a count node). The tree path terminates in a leaf node. Therefore, every path to a leaf node contains an even number of nodes: the root node, the leaf node, and an alternating sequence of count node (keyed by index) and index node (keyed by count). As an example, the 4-dimensional vector [0, 2, 0, 1] would be encoded in the tree as root[1][2][3][1]. The root node would have a count-node child keyed by index 1, which in turn would have an index-node child keyed by count 2, which in turn would have a count-node child keyed by index 3, which in turn would have an index-node child keyed by count 1, which in turn would have a leaf node child.

The Charybdis Tree utilizes a bounded iterator. The goal of the bounded iterator is to perform a traversal through the Charybdis tree that is restricted to traversing only paths that can lead to a leaf node whose path is within a specified Manhattan distance of a specified vector. In other words, it prunes from its traversal all subtrees that cannot possibly contain any leaf nodes satisfying the maximum distance constraint due to the path prefixes leading up to those subtrees already exceeding the constraint.

As illustrated in FIG. 9A, the search process begins with a probe vector (step 810). The tree is descended (812) and it is determined if the maximum Manhattan distance (referred to as the "fuzz") has been exceeded (step 816). If it has, the tree is ascended (step 818) and it is determined if there are more paths to consider (step 814). If there are not, the search process is complete (step 824). If there are the next path is descended into (step 812). If the fuzz was not exceeded, it is determined if a leaf node has been reached (step 820). If so, candidates have been found (step 822) and can be compared. If not, the next level of the tree is descended (step 812).

Figure 9B:
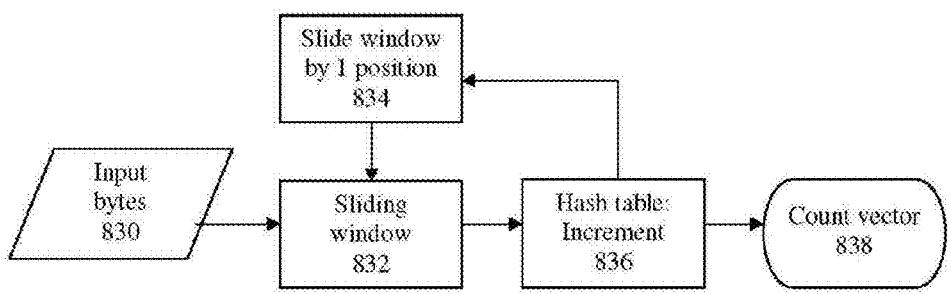
FIG. 9B is a flowchart illustrating steps of a method of vectorizing a Charybdis tree index of stored representative data elements suitable for use in connection with the inventive arrangements disclosed herein.

As illustrated in FIG. 9B, the vectorization process begins with input bytes (830) (typically from an input data element). A sliding window selects bytes from the input (step 832) and the hash table is incremented (step 836). If the window has not reached the end, the window is moved one position (step 834) and the process repeats. If it has reached the end, the result is a count vector (step 838).

More specifically, given (i) a stack containing stack frames, each of which contains a distance adjustment, index node iterator, count node iterator, a target vector, which is the vector being sought by the iteration (i.e., it is the reference vector for Manhattan distance calculations), a cumulative transformation of the target vector, (cum_target), and fuzz (which is the maximum Manhattan distance that leaf nodes returned by the iterator may be from the target vector). Initialization can be performed as follows:

1) Clear the stack.
2) Generate the cum_target vector by setting each element at index i to the sum of all elements in the target vector up to and including the element at index i. For example, a target vector of [2, 1, 3, 1] would produce a cum_target vector of [2, 3, 6, 7].

To find the next leaf node in the traversal:

1) If the stack is empty, then set the active index node to the root node, and set the active index node iterator to the beginning of the root node's children. Otherwise, set the active index node to the node pointed at by the count node iterator in the topmost stack frame, and set the active index node iterator to the end of that index node's children.
2) If the active index node iterator is at the end of the active index node's children, then:
    i. If the stack is empty, then there are no more leaf nodes in the traversal.
    ii. Otherwise, set the active distance adjustment to the distance adjustment in the topmost stack frame, set the active index node iterator to the index node iterator in the topmost stack frame, set the active count node to the node pointed at by the new active index node iterator, set the active count node iterator to the next position after the count node iterator in the topmost stack frame, and pop the stack.
    iii. If the stack is empty, set the active index node to the root node. Otherwise, set the active index node to the node pointed at by the count node iterator in the topmost stack frame.
    iv. Let index be the key of the count node pointed at by the active index node iterator. If index is greater than zero, then set the active distance to the value of the element in cum_target at position index minus one. Otherwise, set the active distance to zero.
3) Otherwise, if the key of the child node pointed at by the active index node iterator is 0xFFFF (meaning the child node is a leaf node), then:
    i. If the stack is empty, then the leaf node is the last leaf node in the traversal.
    ii. Return the leaf node.
4) Otherwise:
    i. Let index be the key of the count node pointed at by the active index node iterator. If index is greater than zero, then set the active distance to the value of the element in cum target at position index minus one. Otherwise, set the active distance to zero.
    ii. If the active distance is greater than fuzz, then:
        1. If the sum of the active distance adjustment and the value of the last element of cum_target is less than or equal to fuzz and the active index node has a child that is a leaf node, then set the active index node iterator to point at that child. Otherwise, set the active index node iterator to point at the end of the active index node's children.
        2. Jump to step 2.
        3. Otherwise, let fuzz_rem equal fuzz minus the active distance. Set the active count node to the count node pointed at by the active index node iterator. If the value of the element of the target vector at position index is less than fuzz_rem, then set the active count node iterator to the beginning of the active count node's children. Otherwise, set the active count node iterator to the first child of the active count node that is greater than or equal to fuzz_rem subtracted from the value of the element of the target vector at position index.
5) Let d be the positive distance between the value of the element of the target vector at position index and the key of the index node pointed at by the active count node iterator. If the active count node iterator is at the end of the active count node's children, or if the sum of the active distance and d is greater than fuzz, then increment the active index node iterator.
6) Otherwise, copy the active distance adjustment, the active index node iterator, and the active count node iterator into a new stack frame and push the new frame onto the stack. Compute d minus the value of the element of the target vector at position index and add the difference to the active distance adjustment. Set the active index node to the index node pointed at by the active count node iterator, and set the active index node iterator to the beginning of the new active index node's children.
7) Jump to step 2.

It can thus been seen how in systems, methods and apparatuses according to the current invention, a neural foam can be used by data analysis manager 136 to perform a correlation of input data elements against previously seen data elements.

Once the data analysis has determined an event operation is to be executed, messages triggering the event operation can be conveyed to the output manager 138. The output manager 138 can be configured to manage the execution of software routines. The output manager 138 can directly execute certain event-related operations. Other event-related operations, however, can be executed by applications 162 remote from the output manager 138. The executed applications 162 can include stand-alone applications or applications distributed across network 160. In one embodiment, the output manager 138 can convey results and/or transaction records pertaining to event operations to the storage manager 134 for recordation purposes. It will be understood by those of ordinary skill in the art that an event operation can be represented by a predetermined set of instructions (such as computer code, commands, remote procedure calls, macros, or the like) executed when the event (typically an association of an input data element with a stored representative data element) has occurred.

Returning to the exemplary network management embodiment illustrated in FIG. 1, the central manager 130 can manage the kernels disposed within a network space 105 to which the central manager 130 is associated. The central manager 130 can function as a communication intermediary between the central database 110 and kernels within the network space 105, conveying data as needed.

By way of illustration, the central manager 130 can be deployed within the network space 105 and conveyed policy enforcement parameters. The central manager 130 can then access the central database 110 to determine profiles and other data necessary to implement the desired network policies. The central manager 130 can start kernels within the network space 105, which can include one or more instances of the input manager 132, the storage manager 134, the data analysis manager 136, and the output manager 138. Each of the kernels can include one or more options and settings that the central manager 130 can adjust to achieve desired behavior.

The central manager 130 can centrally maintain state information of the network space 105. Further, the central manager 130 can convey assignments to the various kernels within the network space 105, these assignments can vary depending upon the state of the network space 105. Further, the central manager 130 can periodically access the central database 110, checking for updates. If updates exist, the central manager 130 can retrieve the updates and convey them to appropriate kernels in the network space 105.

It should be appreciated that the arrangements shown in FIG. 1 are for illustrative purposes only and that the invention is not limited in this regard. The functionality attributable to the various kernels can be combined or separated in different manners than those illustrated herein. For instance, the data analysis manager 136 and the output manager 138 can be implemented as a single software component in another arrangement of the present invention.

In still another arrangement, the central manager 130 can be implemented as more than one kernel. For example, one kernel can manage the state of the network space 105, a separate kernel can handle the configuration of the kernels, and/or a different kernel can manage communications with the central database 110.

It should also be appreciated that processing within system 100 is not necessarily handled in a linear fashion as depicted in FIG. 1. Instead, the kernels of system 100 can establish a flexible and dynamic system where a multitude of interactions occurs between the various kernels. In one arrangement, all other types of kernels can have associated storage manager 134 modules. For example, an input manager 132 module wrapping an application like appSnort can have associated storage manager 134 modules (like storage_cache. storage_db, etc.), the details of which can be determined by analysis requirements and policy. Consequently, in system 100, persistence can be handled in a flexible and independent fashion.

While use of neural foam as described above is preferred, it is not required. FIG. 2A is a schematic diagram illustrating a system 200 that compares network space metrics against factors of a profile in accordance with the inventive arrangements disclosed herein. The system 200 can include a metric data store 210, such as a store managed by the storage manager 134 of FIG. 1. The metrics can be represented as one or more metric tables 225. Each metric table 225 can specify one or more metrics, which together form a footprint of a network usage or event. For each metric in the metric table 225, a metric identifier and value can be specified. Appreciably, metrics in the metric table 225 can be gathered from a multitude of different network components. As can be seen, the metrics need not necessarily be evaluated using a neural foam and, instead, could be analyzed using more traditional techniques.

The system 200 can also include a profile data store 215 that contains profiles that the data analysis manager 136 of FIG. 1 can utilize to determine the occurrence of a network event. Each profile in the profile data store 215 can be represented by a profile table 230. The profile table 230 can include a multitude of metrics, each metric corresponding to a metric of the metric table 225. For example, M1 in the metric table 230 can correspond to M1 in the metric table 225 (M2 to M2, M3 to M3, etc). The profile table 230 can define a normal operating range in which metric values should be within under the profile. For example, a low and a high value can be indicated within the profile table 230.

One or more analysis scripts 220 can be executed to correlate the metric table 225 with a related profile table 230. The analysis scripts 220 can be written in any programming or scripting language, such as Practical Extraction and Reporting Language (PERL), C, JAVA and the like, and will preferably implement a neural foam as has been described. Different event operations (predetermined sets of instructions) can be associated with each event, such as the identification of an association between an input data element and a given representative data element. Other correlation methods can also be used.

FIG. 2B illustrates a table 250 for a peer-to-peer profile in accordance with the inventive arrangements disclosed herein. The table 250 includes columns for factor, predominance, information source, and condition. Factor is a designator for a metric and/or network characteristic. For example, factors for detecting peer-to-peer activity can include, but are not limited to, factors for Port1214, GetString, Point2MP, and/or DNSqueries.

The predominance column of table 250 can represent how indicative the presence of the associated factor is to an event that is to be detected. In one embodiment, the predominance can be a number on a scale, such as 1-10, where 1 can indicates an slight possibility of an occurrence of a profiled event and 10 can be an absolute indication of an occurrence. For example, the Point2MP can be a factor that when detected absolutely indicates an occurrence of a peer-to-peer event. In another example, the DNSqueries factor can be a factor that indicates with a medium certainty that a peer-to-peer even is occurring. Port1214 and GetString can indicate an event with a high certainty.

In one embodiment, predominance factors can include both positive and negative numbers. For example, when particular factors are not present, the lack of presence can be indicative of a non-occurrence of a profiled event. A high degree of accuracy can be achieved when detecting events through multiple, weighted factors. Further, using multiple factors with different predominance characteristics within a profile can make circumventing event detections extremely difficult. For example, even though sophisticated users may be able to hide a domain address and/or initiating address when Web surfing, users cannot hide all metrics characteristic of the activity in which the user is engaged. That is, peer-to-peer file sharing involves contacting many different Web sites in a short time period, downloading large quantities of files often having characteristic file extensions, and the like.

The information source column of table 250 can indicate a network component and/or element associated with a factor. The information source can include any element from which metrics can be gathered. In table 250, illustrative information sources include a srvcRawSocket, appSnort, and appDNSCache.

The condition column of table 250 can indicate a test condition for the factor. A test condition can search a data location and/or file for a particular string, can monitor behavior of a network component, can determine a port being accessed, and the like.

FIG. 2C illustrates a table 260 for a worm detection profile in accordance with the inventive arrangements disclosed herein. The columns of table 260 can include a factor, a predominance, an information source, and a condition, each of which have been previously defined for table 250.

According to table 260, when the appSnort element includes the string "get HTTP/1.1-0d 0a 0d 0a_", then there is a high likelihood that the slapper worm is installed due to a badHTTP factor. A high likelihood of the slapper worm being present is also indicated whenever the appApacheLog-Host144 element contains a string of "client sent HTTP/1.1 request without hostname" or contains a string of "mod_ssl: SSL handshake interrupted by system". Further, an absolute indication of the worm exists when the BadHTP: 1,2 element has a designated time interval characteristic of the worm. Additionally, an absolute indication of the worm exists when the appChkrootkit element contains a string of "Warning Possible Slapper Worm installed."

It should be appreciated that table 250 and table 260 are for illustrative purposes only and that the invention is not to be limited in this regard. That is, profiles can be established for any network event and/or occurrence. Further, any network operation can be executed responsive to the occurrence of the detected event.

It should also be appreciated that the exemplary embodiments described relating to network management are also for illustrative purposes only. In light of the foregoing description, it will be seen that embodiments of systems, methods, and apparatuses according to the present invention can be adapted to a wide variety of applications in which it is desirable to categorize a large set of date elements or analyze and characterize a set of streamed data elements in real time. Examples of such applications include, but are not limited to, analyzing network traffic on a computer network (including detecting intrusions, identifying inappropriate uses, and analyzing usage trends), analyzing messaging system messages (such as text messages or email messages) to identify patterns and commonalities based on similarities among messages (and potentially taking specific actions when new messages are identified that are likely to have characteristics in common with stored representative messages), analyzing large data files (including without limitation text-based log files) to identify commonalities between groups of entries, analyzing large graphs (including without limitations graphs of the structure of a social network or a computation graph for a distributed system), analyzing databases containing large amounts of data in tables or returned by queries, for common patterns, and analyzing electronic representations of physical items (such as DNA molecules or the structure of a social network) to identify commonalities and patterns in such physical items. The incremental learning aspect of preferred embodiments of systems, methods, and apparatuses of the present invention are particularly well suited to applications in which a continuously evolving data set is to be analyzed. Whereas prior art solutions required either storing the entire data set prior to analysis, or pre-training a system to identify certain patterns, embodiments of the present invention are adapted to receiving streams of input data elements in real time and learning incrementally such that new patterns are identified without the necessity of pre-training.

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein may be utilized. A typical combination of hardware and software can be a general-purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. "Computer program" in the present context means any expression, in any language, code or notation, of a set of instructions intended to cause a system having an information processing capability to perform a particular function either directly or after either or both of the following: a) conversion to another language, code or notation; b) reproduction in a different material form.

Figure 3:
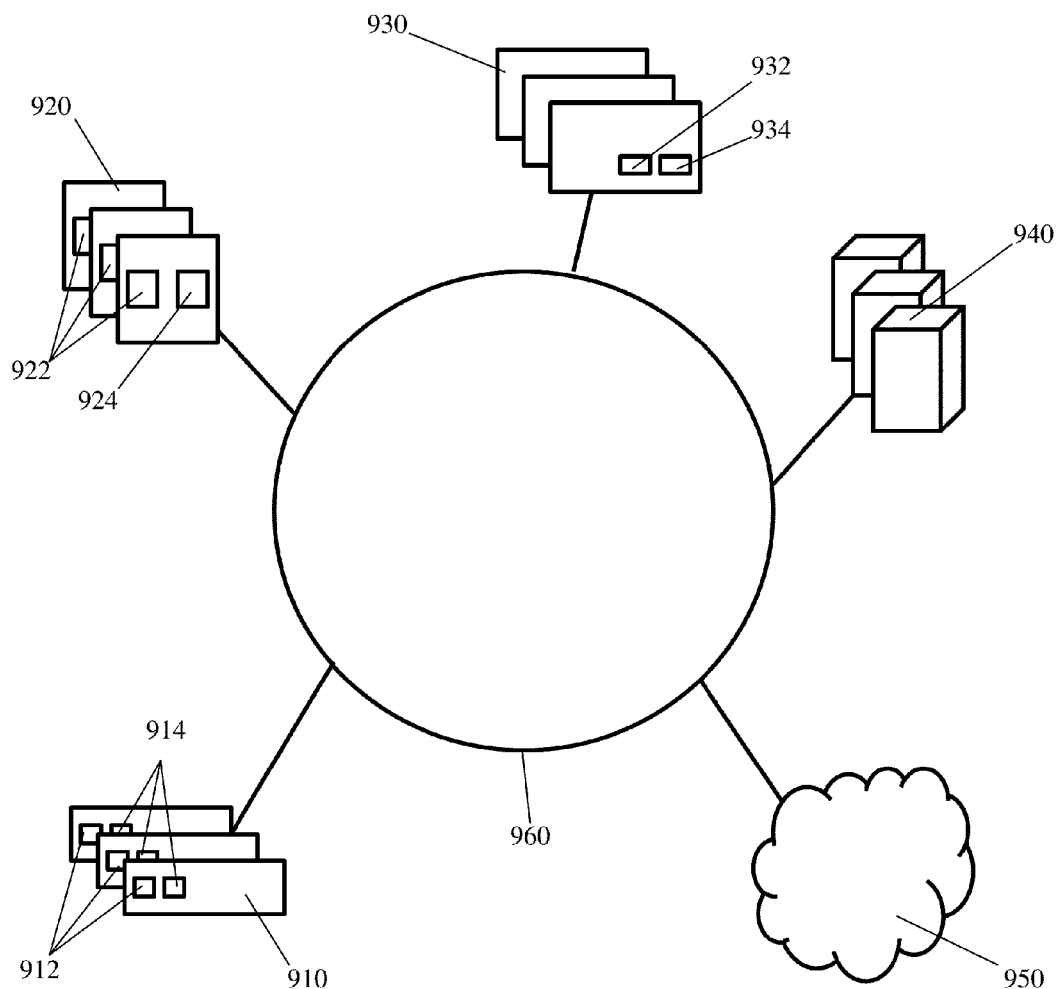
FIG. 3 is a schematic diagram illustrating components of an embodiment of an incrementally-learning data classification system in accordance with the inventive arrangements disclosed herein.

In sum, referring to FIG. 3, a preferred embodiment of the system of the present invention is an incrementally learning data classification system comprising at least one specially-programmed server 910 comprising a processor 912 and at least one machine-readable storage 914. The server is operably connected to a computer network 960. Processor 912 is adapted to receive input data elements from the computer network 960, compute a distance between the input data elements and a plurality of representative data elements stored in the machine-readable storage 914 and compare the input data elements to the representative data elements based on a threshold value. It will be understood that the representative data elements or sufficient representations thereof may be retrieved from a database (not illustrated), and in some cases a distributed database (not illustrated), prior to being stored in machine-readable storage 914. Alternatively, machine-readable storage 914 may itself be adapted to operate as a database or a distributed database.

Where the distance between one of the representative data elements and the input data element is less than the threshold value, processor 912 executes a predetermined set of instructions corresponding to the representative data element. Where the distance between the input data element and all representative data elements is not less than the threshold value, processor 912 stores the input data element in the at least one machine-readable storage 914 as a new representative data element, and may also store such representative data element in a database (not illustrated) or a distributed database (not illustrated). Processor 912 is further adapted to output associations of input data elements and representative data elements based on the distance being less than the threshold value. The associations thus represent categorizations of input data elements and representative data elements into sets based on common properties. The input data elements are thereby classified based on the associations output by processor 912.

FIG. 3 also can be seen to illustrate a further preferred embodiment that provides an incrementally learning data processing system for classifying data elements. The data processing system comprises at least one computer processor means for processing data. In this context, a computer processor means could be a hardware microprocessor or CPU 912 in a computer adapted to be a server 910. It could also be a hardware microprocessor or CPU 922, 932 in a network device such as a router 920 or other network device 930 (such as, for example, a switch, gateway, bridge, network attached security device or network attached storage device). It could also be a microprocessor or CPU (not illustrated) on a workstation, laptop, or tablet computing device (jointly illustrated as 940), also operably connected to network 960, or a processor or custom logic circuit within a custom hardware device that is adapted to stand alone as a network device or that is adapted to be included within one of the aforementioned (not illustrated). Computer processor means 912, 922, 932 is operably connected to a computer network 916 such that it can receive input data elements from network 960. At least one storage means (914, 924, 934) for storing data available for processing by said at least one computer processor means on a machine readable medium. Herein, storage means 914, 924, 934 can include, respectively, a random access memory or hard drive within server 910, or a detachable or other machine-readable storage operably connected to server 910; a random access memory or hard drive within router 920 or a detachable or other machine-readable storage operably connected to router 920; a random access memory or hard drive within network device 930 or a custom hardware device, or a detachable or other machine-readable storage operably connected thereto. It could also include a random access memory or hard drive within computing device 940 or a detachable or other machine-readable storage operably connected to computing device 940.

At least one first means for receiving input data elements from computer network 960 is provided. The first means may be an arithmetic circuit, processor or CPU adapted to selectively store and retrieve binary data from a machine-readable storage. Processor 912, 922, 932 may each be adapted to serve as the first means for receiving input data, as could any of the processing means previously described. Alternatively, a separate CPU or custom logic circuit could be used. At least one second means for computing a distance between the input data elements and a plurality of representative data elements stored in the at least one storage means and comparing the input data elements to said representative data elements based on a threshold value is also provided. The second means may also be an arithmetic or logic circuit, processor or CPU adapted to selectively store and retrieve binary data from a machine-readable storage, and processor 912, 922, 932 and the other processor means previously described may each be further adapted to serve as the second means.

Where the distance between one of the representative data elements and the input data element is less than the threshold value, the second means causes a predetermined set of instructions corresponding to the representative data element to be performed. Where the distance between the input data element and the representative data elements is not less than the threshold value, the second means stores the input data element in the at least one machine-readable storage as a new representative data element. In this way, performance of the set of instructions corresponding to the representative data element classifies the input data element as being associated with the representative data element.

FIG. 4 illustrates a preferred embodiment of a method of classifying network traffic according to the present invention. The method comprises providing at least one specially-programmed server comprising a processor and at least one machine-readable storage, the server being operably connected to a computer network (step 610). Further steps comprise causing the server to receive input data elements from network traffic on the computer network (step 612); compute a distance between the input data elements and a plurality of representative data elements stored in the machine-readable storage (step 616) and compare the input data elements to the representative data elements based on a threshold value (618). As has been discussed, the representative elements may optionally be retrieved from a database or distributed database prior to be being stored in the machine-readable storage for analysis. Alternatively, the machine-readable storage itself may be adapted to serve as a database or a distributed database.

Where the distance between one of the representative data elements and the input data element is less than the threshold value, the processor is caused to associate the input data element with the representative data element (step 620) and execute a predetermined set of instructions indicating and/or responding to such association (step 622). Where the distance between the input data element and all representative data elements is not less than the threshold value (step 624), the processor is caused to store the input data element in the at least one machine-readable storage as a new representative data element (step 626) and optionally output the associations of the input data elements and the representative data elements based on the distance being less than the threshold value. In this way, associations represent categorizations of the input data elements based on common properties. Network traffic is thus classified based on the output associations such that traffic associated with each representative data element is grouped according the same classification.

Figure 5:
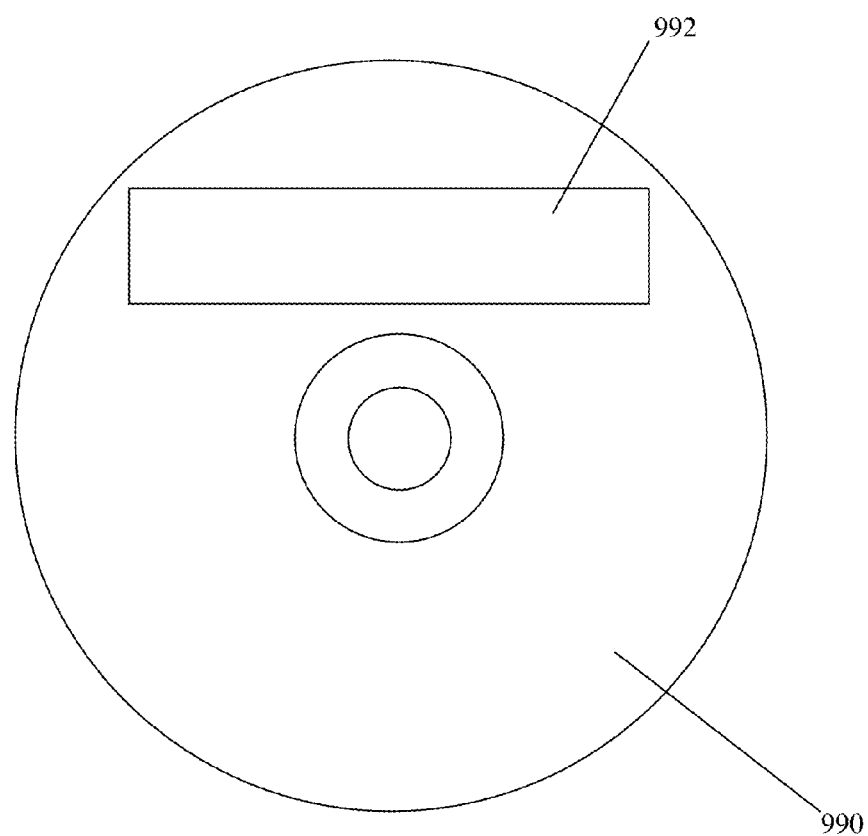
FIG. 5 is a schematic diagram illustrating an embodiment of a machine-readable storage medium in accordance with the inventive arrangements disclosed herein.

FIG. 5 illustrates a machine-readable storage medium 990 containing instructions 992 to cause a specially programmed server operably connected to a computer network to perform a method of classifying traffic on the computer network. The method comprises the steps of receiving input data elements from the network traffic; computing a distance between the input data elements and a plurality of representative data elements stored in machine-readable storage and comparing the input data elements to said representative data elements based on a threshold value. Where the distance between one of the representative data elements and the input data element is less than the threshold value, the input data element is associated with the representative data element. Where the distance between the input data element and the representative data elements is not less than the threshold value, the input data element is stored in the machine-readable storage as a new representative data element. Further steps implemented in instructions 992 comprise outputting associations of the input data elements and the representative data elements to a computer user based on the distance being less than the threshold value, thereby categorizing the input data element and the representative data elements based on common properties. In this way, network traffic is classified based on the associations output such that traffic categorized with each said representative data element is grouped according the same classification. Whereas machine-readable storage medium 990 is illustrated as a CD or DVD, it will be understood that any machine-readable storage medium (as defined herein) may be utilized. The shape and location of the schematic representation of instructions 992 is not intended to represent the physical layout of such instructions on the media.

Figure 10:
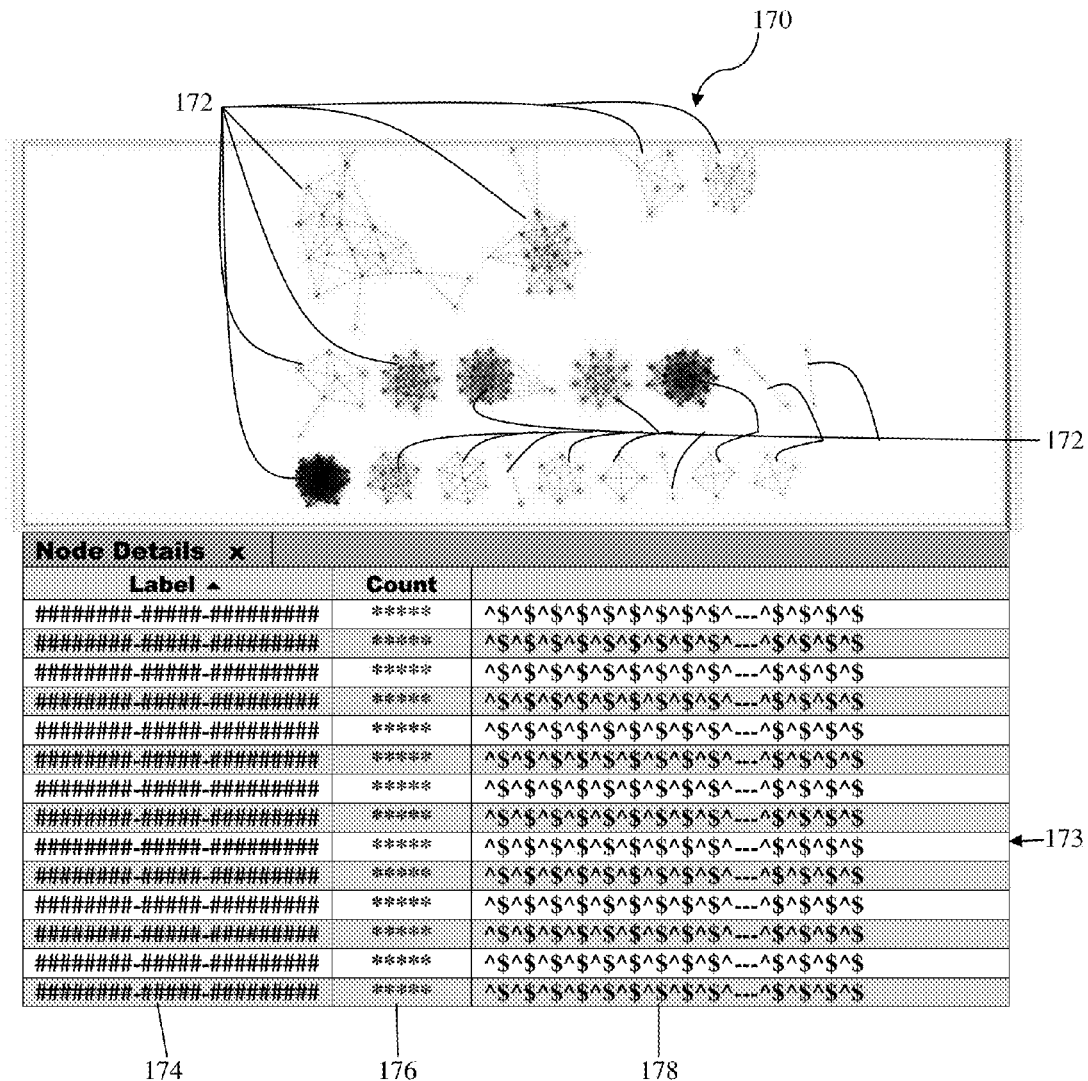
FIG. 10 is a schematic diagram of an output of associations of representative data elements in accordance with the inventive arrangements disclosed herein.

FIG. 10 illustrates a visualization system displaying the contents of neural foam developed with a preferred embodiment of a system according to the present invention. In visualization area 170, nodes in the figure represent nodes in a Cartesian/Manhattan-distance-based neural foam, with connected nodes representing clusters 172 that have been determined to have some commonality. When a particular cluster of nodes 172 is selected, a table 173 below the visualization shows a label 174 and count 176 for each node in the cluster, together with the data 178 corresponding to that node. Lines between nodes indicate an association between closest nodes. The label 174, which may be a globally unique identifier or GUID (which may be calculated by means well known in the art) is assigned to the node for reference purposes. The count 176 indicates the number of input data elements that have been found to be within a threshold distance of that node. It is thus apparent that not every input is stored as a node in the foam. Instead, only nodes representative of groups of highly similar inputs are stored. By selecting one cluster 172, a user may identify representative data elements within such cluster. By selecting a label 174, information identifying input data elements associated with such representative data element could be retrieved, if such information was stored as part of a set of predetermined instructions. It is important to note, however, that this is just one possible means of outputting associations and several other suitable means of outputting such associations will also be apparent to those of ordinary skill in the art based on the foregoing description, including those elsewhere identified herein.

As will be understood by those of ordinary skill in the art, this invention can be embodied in other forms without departing from the spirit or essential attributes thereof. Accordingly, reference should be made to the following claims, rather than to the foregoing specification, as indicating the scope of the invention.

We claim:

1. An incrementally learning data classification system comprising at least one specially-programmed server comprising a processor and at least one machine-readable storage, said server being operably connected to a computer network, wherein said processor is adapted to:
  a. receive input data elements from said computer network;
  b. compute a normalized compression distance between said input data elements and a plurality of representative data elements stored in said machine-readable storage and compare said input data elements to said representative data elements based on a threshold value such that
    (i) where the normalized compression distance between one of said representative data elements and said input data element is less than said threshold value, said processor executes a predetermined set of instructions corresponding to said representative data element, and
    (ii) where the normalized compression distance between said input data element and all said representative data elements is not less than said threshold value said processor stores said input data element in said at least one machine-readable storage as a new representative data element, and
  c. said processor is further adapted to output associations of said input data elements and said representative data elements based on said normalized compression distance being less than said threshold value wherein said associations represent categorizations of said input data elements and said representative data elements based on common properties;
  whereby said input data elements are classified based on said associations output by said processor.

2. The system of claim 1 wherein said processor is further adapted to compute said normalized compression distance using a lossy compression.

3. The system of claim 2 wherein said computation of said normalized compression distance between said input data elements and said plurality of representative data elements comprises
  (a) determining the compressed length of the concatenation of said input data element and said representative data element,
  (b) subtracting from said compressed length of said concatenation of said input data element and said representative data element the lesser of the compressed length of said input data element and the compressed length of said representative data element, and
  (c) dividing said subtracted value by the greater of said compressed length of said input data element and said compressed length of said representative data element.

4. The system of claim 2 wherein said computation of said normalized compression distance between said input data elements and said plurality of representative data elements comprises
  (a) determining the compressed length of the concatenation of said input data element and said representative data element,
  (b) subtracting from said compressed length of said concatenation of said input data element and said representative data element the lesser of the compressed length of said input data element concatenated to itself and the compressed length of said representative data element concatenated to itself, and
  (c) dividing said subtracted value by the greater of said compressed length of said input data element concatenated to itself and said compressed length of said representative data element concatenated to itself.

5. The system of claim 1 wherein said data elements are packets of network data.

6. The system of claim 1 wherein said data elements are message service messages on a wide area communications network.

7. The system of claim 6 wherein said message service messages are text messages.

8. The system of claim 1 wherein said data elements comprise requests for web pages and responses to said requests.

9. The system of claim 1 wherein said processor is further adapted to store said associations in a distributed database.

10. The system of claim 1 wherein said processor is further adapted to store said representative data elements in said at least one machine readable storage in a tree structure.

11. The system of claim 10 wherein said tree structure is a dispersion tree.

12. An incrementally learning data processing system for classifying data elements comprising:
  a. at least one computer processor means for processing data, said computer processor means being operably connected to a computer network;
  b. at least one storage means for storing data available for processing by said at least one computer processor means on a machine readable medium;
  c. at least one first means for receiving input data elements from said computer network;
  d. at least one second means for computing a normalized compression distance between said input data elements and a plurality of representative data elements stored in said at least one storage means and comparing said input data elements to said representative data elements based on a threshold value such that
    (i) where the normalized compression distance between one of said representative data elements and said input data element is less than said threshold value, said second means causes a predetermined set of instructions corresponding to said representative data element to be performed, and
    (ii) where the normalized compression distance between said input data element and said representative data elements is not less than said threshold value said second means stores said input data element in said at least one machine-readable storage as a new representative data element, whereby performance of said set of instructions corresponding to said representative data element classifies said input data element as being associated with said representative data element.

13. The system of claim 12 wherein said at least one second means computes said normalized compression distance using a lossy compression.

14. The system of claim 13 wherein said at least one second means is adapted to compute said normalized compression distance between said input data elements and said plurality of representative data elements by
   (a) determining the compressed length of the concatenation of said input data element and said representative data element,
   (b) subtracting from said compressed length of said concatenation of said input data element and said representative data element the lesser of the compressed length of said input data element and the compressed length of said representative data element, and
   (c) dividing said subtracted value by the greater of said compressed length of said input data element and said compressed length of said representative data element.

15. The system of claim 13 wherein said at least one second means is adapted to compute said normalized compression distance between said input data elements and said plurality of representative data elements by
   (a) determining the compressed length of the concatenation of said input data element and said representative data element,
   (b) subtracting from said compressed length of said concatenation of said input data element and said representative data element the lesser of the compressed length of said input data element concatenated to itself and the compressed length of said representative data element concatenated to itself, and
   (c) dividing said subtracted value by the greater of said compressed length of said input data element concatenated to itself and said compressed length of said representative data element concatenated to itself.

16. The system of claim 12 wherein said data elements are packets of network data.

17. The system of claim 12 wherein said data elements are message service messages on a wide area communications network.

18. The system of claim 12 wherein said data elements comprise requests for web pages and responses to said requests.

19. The system of claim 12 wherein said at least one storage means comprises a plurality of machine readable mediums accessed by a distributed database.

20. The system of claim 12 wherein said representative data elements are stored in said at least one storage means in a tree structure.

21. The system of claim 20 wherein said tree structure is a dispersion tree.

22. A method of classifying network traffic comprising:
   a. providing at least one specially-programmed server comprising a processor and at least one machine-readable storage, said specially-programmed server being operably connected to a computer network,
   b. causing said at least one specially-programmed server to
      (i) receive input data elements from network traffic on said computer network;
      (ii) compute a normalized compression distance between said input data elements and a plurality of representative data elements stored in said machine-readable storage and compare said input data elements to said representative data elements based on a threshold value such that
      where the normalized compression distance between one of said representative data elements and said input data element is less than said threshold value, said processor associating said input data element with said representative data element, and
      where the normalized compression distance between said input data element and all said representative data elements is not less than said threshold value said processor stores said input data element in said at least one machine-readable storage as a new representative data element, and
      c. outputting associations of said input data elements and said representative data elements based on said normalized compression distance being less than said threshold value wherein said associations represent categorizations of said input data elements based on common properties;
   whereby said network traffic is classified based on said output associations such that traffic associated with each said representative data element is grouped according the same classification.

23. The method of claim 22 further comprising the step of computing said normalized compression distance using a lossy compression.

24. The method of claim 23 wherein said normalized compression distance between said input data elements and said plurality of representative data elements is computed by
   (a) determining the compressed length of the concatenation of said input data element and said representative data element,
   (b) subtracting from said compressed length of said concatenation of said input data element and said representative data element the lesser of the compressed length of said input data element and the compressed length of said representative data element, and
   (c) dividing said subtracted value by the greater of said compressed length of said input data element and said compressed length of said representative data element.

25. The method of claim 23 wherein said normalized compression distance between said input data elements and said plurality of representative data elements is computed by
   (a) determining the compressed length of the concatenation of said input data element and said representative data element,
   (b) subtracting from said compressed length of said concatenation of said input data element and said representative data element the lesser of the compressed length of said input data element concatenated to itself and the compressed length of said representative data element concatenated to itself, and
   (c) dividing said subtracted value by the greater of said compressed length of said input data element concatenated to itself and said compressed length of said representative data element concatenated to itself.

26. The method of claim 22 wherein said data elements received from said network traffic are message service messages on a wide area communications network.

27. The method of claim 22 wherein said data elements received from said network traffic are requests for web pages and responses to said requests.

28. The method of claim 22 wherein said machine-readable storage comprises a plurality of machine readable mediums accessed by a distributed database.

29. The method of claim 22 further comprising the step of storing said representative data elements in said machine-readable storage in a tree structure.

30. The method of claim 29 wherein said tree structure is a dispersion tree.

31. An incrementally learning data classification system comprising at least one specially-programmed server comprising a processor and at least one machine-readable storage, said server being operably connected to a computer network, wherein said processor is adapted to:
(a) receive input data elements from said computer network;
(b) compute a plurality of metrics for each said input data element;
(c) compute a Manhattan distance based on said plurality of metrics between said input data elements and a plurality of representative data elements stored in said machine-readable storage and compare said input data elements to said representative data elements based on a threshold value such that
  (i) where the distance between one of said representative data elements and said input data element is less than said threshold value, said processor executes a predetermined set of instructions corresponding to said representative data element, and
  (ii) where the distance between said input data element and all said representative data elements is not less than said threshold value, said processor stores said input data element in said at least one machine-readable storage as a new representative data element and forms an association between said new representative data element and at least one closest stored representative data element; and
(c) said processor is further adapted to output associations of said input data elements and said representative data elements based on said distance being less than said threshold value wherein said associations represent categorizations of said input data elements and said representative data elements based on common properties;
whereby said input data elements are classified based on said associations output by said processor.

32. The system of claim 31 wherein said data elements are packets of network data.

33. The system of claim 31 wherein said data elements are message service messages on a wide area communications network.

34. The system of claim 33 wherein said message service messages are text messages.

35. The system of claim 31 wherein said data elements comprise requests for web pages and responses to said requests.

36. The system of claim 31 wherein said processor is further adapted to store said representative data elements and said associations in a distributed database.

37. The system of claim 31 wherein said processor is further adapted to store said representative data elements in said at least one machine readable storage in a tree structure.

38. The system of claim 37 wherein said tree structure is a Charybdis tree.

39. An incrementally learning data processing system for classifying data elements comprising:
(a) at least one computer processor means for processing data, said computer processor means being operably connected to a computer network;
(b) at least one storage means for storing data available for processing by said at least one processor on a machine readable medium;
(c) at least one first means for receiving input data elements from said computer network and computing a plurality of metrics from said input data elements;
(d) at least one second means for computing a Manhattan distance based on said metrics between said input data elements and a plurality of representative data elements stored in said at least one storage means and comparing said input data elements to said representative data elements based on a threshold value such that
  (i) where the distance between one of said representative data elements and said input data element is less than said threshold value, said second means causes a predetermined set of instructions corresponding to said representative data element to be performed, and
  (ii) where the distance between said input data element and said representative data elements is not less than said threshold value said second means stores said input data element in said at least one machine-readable storage as a new representative data element and stores an association between said new representative data element and at least one closest stored representative data element,
whereby performance of said set of instructions corresponding to said representative data element classifies said input data element as being associated with said representative data element.

40. The system of claim 39 wherein said input data elements are packets of network data.

41. The system of claim 39 wherein said input data elements are message service messages on a wide area communications network.

42. The system of claim 39 wherein said input data elements comprise requests for web pages and responses to said requests.

43. The system of claim 39 wherein said at least one storage means comprises a plurality of machine-readable mediums adapted to be accessed by a distributed database.

44. The system of claim 39 wherein said representative data elements are stored in said at least one storage means in a tree structure.

45. The system of claim 44 wherein said tree structure is a Charybdis tree.

46. A method of classifying network traffic comprising:
(a) providing at least one specially-programmed server comprising a processor and at least one machine-readable storage, said at least one specially-programmed server being operably connected to a computer network;
(b) causing said at least one specially-programmed server to
  (i) receive input data elements from network traffic on said computer network and calculate a plurality of metrics from each said input data element,
  (ii) compute a Manhattan distance based on said metrics between said input data elements and a plurality of representative data elements stored in said machine-readable storage and compare said input data elements to said representative data elements based on a threshold value such that
where the distance between one of said representative data elements and said input data element is less than said threshold value, said processor associates said input data element with said representative data element, and
where the distance between said input data element and all said representative data elements is not less than said threshold value said processor stores said input data element in said at least one machine-readable storage as a new representative data element and stores at least one association between said new representative data element and the closest said stored data representative data element; and (c) further causing said at least one specially-programmed server to output associations of said input data elements and said representative data elements based on said compression distance being less than said threshold value wherein said associations represent categorizations of said input data elements based on common properties;

whereby said network traffic is classified based on said output associations such that traffic associated with each said representative data element is grouped according the same classification.

47. The method of claim 46 wherein said data elements received from said network traffic are message service messages on a wide area communications network.

48. The method of claim 46 wherein said data elements received from said network traffic are requests for web pages and responses to said requests.

49. The method of claim 46 wherein said machine-readable storage comprises a plurality of machine readable mediums accessed by a distributed database.

50. The method of claim 46 further comprising the step of storing said representative data elements in said machine-readable storage in a tree structure.

51. The method of claim 50 wherein said tree structure is a Charybdis tree.

* * * * *